(12) United States Patent
Menon et al.

(10) Patent No.: US 10,099,214 B2
(45) Date of Patent: Oct. 16, 2018

(54) ZIRCONIUM PHOSPHATE AND ZIRCONIUM OXIDE RECHARGER CONTROL LOGIC AND OPERATIONAL PROCESS ALGORITHMS

(71) Applicant: Medtronic, Inc., Minneapolis, MN (US)

(72) Inventors: Kanjimpuredathil Muralikrishna Menon, Bangalore (IN); Sujeendran Malayath, Bangalore (IN); Martin T. Gerber, Maple Grove, MN (US); Christopher M. Hobot, Tonka Bay, MN (US); Kaustubh R. Patil, Bangalore (IN); Ramkumar Jeyachandran, Bangalore (IN); Sameer Saxena, Gwalior (IN)

(73) Assignee: Medtronic, Inc., Minneapolis, MN (US)

( * ) Notice: Subject to any disclaimer, the term of this patent is extended or adjusted under 35 U.S.C. 154(b) by 315 days.

(21) Appl. No.: 15/143,494

(22) Filed: Apr. 29, 2016

(65) Prior Publication Data

US 2016/0243540 A1 Aug. 25, 2016

Related U.S. Application Data

(63) Continuation-in-part of application No. 14/722,068, filed on May 26, 2015, and a continuation-in-part of
(Continued)

(51) Int. Cl.
*B01J 49/75* (2017.01)
*B01J 49/00* (2017.01)
(Continued)

(52) U.S. Cl.
CPC .......... *B01J 49/0073* (2013.01); *A61M 1/169* (2013.01); *A61M 1/1696* (2013.01);
(Continued)

(58) Field of Classification Search
None
See application file for complete search history.

(56) References Cited

U.S. PATENT DOCUMENTS 3,840,835 A 11/1974 Marantz
3,850,835 A 11/1974 Marantz
(Continued)

FOREIGN PATENT DOCUMENTS

CN 1487853 A 11/2000
EP 2446908 5/2012
(Continued)

OTHER PUBLICATIONS

PCT/US2015/019901 International Search Report and Written Opinion dated Jun. 5, 2015.
(Continued)

*Primary Examiner* — Richard C Gurtowski
(74) *Attorney, Agent, or Firm* — Kenneth Collier; Roger Hahn

(57) ABSTRACT

Control logic and processes for monitoring and controlling sorbent rechargers are presented. The control logic and processes use control systems to monitor the rechargers for performance problems and to control the recharging process. Various sensors in communication with the control systems are provided to ensure proper operation.

19 Claims, 20 Drawing Sheets

Related U.S. Application Data application No. 14/722,119, filed on May 26, 2015, which is a continuation-in-part of application No. 14/642,847, filed on Mar. 10, 2015, now Pat. No. 9,974,896, and a continuation-in-part of application No. 14/261,651, filed on Apr. 25, 2014, now Pat. No. 9,895,477, said application No. 14/722,068 is a continuation-in-part of application No. 14/642,847, and a continuation-in-part of application No. 14/261,651.

(60) Provisional application No. 62/077,159, filed on Nov. 7, 2014, provisional application No. 62/016,613, filed on Jun. 24, 2014, provisional application No. 61/941,672, filed on Feb. 19, 2014, provisional application No. 61/909,372, filed on Nov. 26, 2013.

(51) Int. Cl.
| | | |
|---|---|---|
| *A61M 1/16* | (2006.01) | |
| *B01J 41/02* | (2006.01) | |
| *B01J 20/34* | (2006.01) | |
| *B01J 20/02* | (2006.01) | |
| *B01J 39/12* | (2006.01) | |
| *B01J 20/06* | (2006.01) | |

(52) U.S. Cl.
CPC ....... *B01J 20/0211* (2013.01); *B01J 20/0292* (2013.01); *B01J 20/06* (2013.01); *B01J 20/3475* (2013.01); *B01J 20/3483* (2013.01); *B01J 39/12* (2013.01); *B01J 41/02* (2013.01); *A61M 2205/3317* (2013.01); *A61M 2205/3324* (2013.01); *A61M 2205/3331* (2013.01); *A61M 2205/3334* (2013.01); *A61M 2205/3368* (2013.01)

(56) References Cited

U.S. PATENT DOCUMENTS

| | | |
|---|---|---|
| 4,192,748 A | 3/1980 | Hyden |
| 4,687,582 A | 8/1987 | Dixon |
| 6,579,460 B1 | 6/2003 | Willis |
| 2002/0112609 A1 | 8/2002 | Wong |
| 2003/0097086 A1 | 5/2003 | Gura |
| 2005/0056592 A1 | 3/2005 | Braunger |
| 2005/0274658 A1 | 12/2005 | Rosenbaum |
| 2006/0241543 A1 | 10/2006 | Gura |
| 2008/0011664 A1 | 1/2008 | Karoor |
| 2008/0241031 A1 | 10/2008 | Li |
| 2009/0101552 A1 | 4/2009 | Fulkerson |
| 2009/0282980 A1 | 11/2009 | Gura |
| 2010/0004588 A1 | 1/2010 | Yeh |
| 2010/0078387 A1 | 4/2010 | Wong |
| 2010/0312172 A1 | 12/2010 | Hoffman |
| 2011/0017665 A1 | 1/2011 | Updyke |
| 2011/0048949 A1 | 3/2011 | Ding et al. |
| 2011/0171713 A1 | 7/2011 | Bluchel |
| 2011/0272352 A1 | 11/2011 | Braig |
| 2011/0297593 A1 | 12/2011 | Kelly |
| 2012/0273354 A1 | 11/2012 | Orhan et al. |
| 2013/0199998 A1 | 8/2013 | Kelly |
| 2013/0213890 A1 | 8/2013 | Kelly |
| 2014/0158588 A1 | 6/2014 | Pudil |
| 2014/0158623 A1 | 6/2014 | Pudil |
| 2015/0108069 A1 | 4/2015 | Merchant |
| 2015/0251161 A1 | 9/2015 | Pudil |
| 2015/0251162 A1 | 9/2015 | Pudil |
| 2015/0367055 A1 | 12/2015 | Pudil |

FOREIGN PATENT DOCUMENTS

| | | |
|---|---|---|
| JP | S5070281 A | 6/1975 |
| JP | S5070281 A | 6/1975 |
| JP | S51-55193 | 5/1976 |
| JP | S61164562 | 7/1986 |
| JP | 2981573 | 11/1999 |
| JP | 2005511250 | 4/2005 |
| JP | 2007-44602 A | 2/2007 |
| JP | 200744602 | 2/2007 |
| JP | 200744602 A | 2/2007 |
| JP | 200744602 A | 2/2007 |
| JP | 2013502987 | 1/2013 |
| WO | WO 2011/017215 | 2/2011 |
| WO | WO 2013/019994 | 2/2013 |
| WO | WO 2013-025957 | 2/2013 |
| WO | WO 2013-028809 | 2/2013 |
| WO | WO 2013019179 | 2/2013 |
| WO | 2013101888 | 7/2013 |
| WO | WO 2013/103607 | 7/2013 |
| WO | 2015060914 | 4/2015 |
| WO | 2015199765 | 12/2015 |
| WO | 2015199863 | 12/2015 |
| WO | 2015199864 | 12/2015 |

OTHER PUBLICATIONS

PCT/US2015/032492 International Search Report dated Nov. 19, 2015.
PCT/US2015/032492 Written Opinion dated Nov. 19, 2015.
Wheaton, et al., Dowex Ion Exchange Resins—Fundamentals of Ion Exchange; Jun. 2000, pp. 1-9. http://www.dow.com/scripts/litorder.asp?filepath=liquidseps/pdfs/noreg/177-01837.pdf.
PCT/US2016/030319 Written Opinion dated Jul. 27, 2016.
Office Action in App. No. AU 2015280604 dated Apr. 8, 2016.
Wester et al., A regenerable postassium and phosphate sorbent system to enhance dialysis efficacy and device portability: an in vitro study Nephrol Dial Transplant (2013) 28: 2364-2371 Jul. 3, 2013.
John Wm Agar: "Review: Understanding sorbent dialysis systems," Nephrology, vol. 15, No. 4, Jun. 1, 2010, pp. 406-411.
Office Action in App. No. JP 2016-515476 dated Dec. 26, 2016.
Japanese Patent Publication No. S50-70281A.
Japanese Patent Publication No. 2007-44602A.
PCT/US2015/032494 Written Opinion dated Nov. 19, 2015.
PCT/US2015/032494 International Search Report dated Nov. 19, 2015.
PCT/US2015/019901 International Preliminary Report on Patentability dated May 27, 2016.
PCT/US2015/019901 Written Opinion dated May 27, 2016.
PCT/US2015/019901 Written Opinion dated Jun. 5, 2015.
PCT/US2015/019901 International Search Report dated Jun. 5, 2015.
PCT/US2015/032485 International Preliminary Report on Patentability dated May 11, 2016.
PCT/US20115/032485 International Preliminary Report on Patentability dated May 11, 2016.
PCT/US2016/030304 International Search Report dated Jul. 27, 2016.
PCT/US2016/030304 Written Opinion dated Jul. 27, 2016.
PCT/US2016/030312 Written Opinion dated Jul. 28, 2016.
PCT/US2016/030312 International Search Report dated Jul. 28, 2016.
PCT/US2016/030319 International Search Report dated Jul. 27, 2016.
PCT/US2016/030320 International Search Report dated Jul. 28, 2016.
PCT/US2016/030320 Written Opinion dated Jul. 28, 2016.
PCT/US2015/032485 Written Opinion dated May 9, 2016.
PCT/US2015/032485 Written Opinion dated Oct. 16, 2015.
PCT/US2016/030320 International Preliminary Report on Patentability, dated Apr. 20, 2017.
European Search Report and Supplemental Search Report in European Application No. 14865374.4 dated Jun. 12, 2017.
[NPL696] PCT/US2015/032485 Written Opinion dated May 9, 2016.
European Search Report for EP App. No. 15811326.6, dated Feb. 12, 2018.

(56) References Cited

OTHER PUBLICATIONS

European Search Report for EP App. No. 15812413.1, dated Feb. 2, 2018.
PCT/US2016/030319_IPRP.
Search Report in EP App. No. 15752771, dated Nov. 22, 2017.
[NPL721] PCT/US2015/019901 International Preliminary Report on Patentability dated May 27, 2016.
[NPL720] PCT/US2015/019901 International Search Report and Written Opinion dated Jun. 5, 2015.
[NPL756] European Search Report and Supplemental Search Report in European Application No. 14865374.4 dated Jun. 12, 2017.
[NPL722] PCT/US2015/032494 International Preliminary Report on Patentablity dated Dec. 27, 2016.
[NPL10] Wheaton, et al., Dowex Ion Exchange Resins—Fundamentals of Ion Exchange; Jun. 2000, pp. 1-9. http://www.dow.com/scripts/litorder.asp?filepath=liquidseps/pdfs/noreg/177-01837.pdf.
[NPL591] PCT/US2016/030320 Written Opinion dated Jul. 27, 2016.
[NPL603] Japanese Patent Publication No. S50-70281A.
[NPL602] Office Action in App. No. JP 2016-515476 dated Dec. 26, 2016.
[NPL605] PCT/US2015/032494 Written Opinion dated Nov. 19, 2015.
[NPL606] PCT/US2015/032494 International Search Report dated Nov. 19, 2015.
[NPL608] PCT/US2015/019901 Written Opinion dated May 27, 2016.
[NPL609] PCT/US2015/019901 Written Opinion dated Jun. 5, 2015.
[NPL622] PCT/US2015/032485 Written Opinion dated Oct. 16, 2015.
[NPL611] PCT/US2015/032485 International Preliminary Report on Patentability dated May 11, 2016.
[NPL612] PCT/US2015/032485 International Preliminary Report on Patentability dated May 11, 2016.
[NPL613] PCT/US20115/032485 International Preliminary Report on Patentability dated May 11, 2016.
[NPL615] PCT/US2016/030304 Written Opinion dated Jul. 27, 2016.
[NPL616] PCT/US2016/030312 Written Opinion dated Jul. 28, 2016.
[NPL617] PCT/US2016/030312 International Search Report dated Jul. 28, 2016.
[NPL618] PCT/US2016/030319 International Search Report dated Jul. 27, 2016.
[NPL619] PCT/US2016/030319 Written Opinion dated Jul. 27, 2016.
[NPL607] PCT/US2015/019901 International Preliminary Report on Patentability dated May 27, 2016.
[NPL610] PCT/US2015/019901 International Search Report dated Jun. 5, 2015.
[NPL621] PCT/US2016/030320 International Search Report dated Jul. 28, 2016.
[NPL623] PCT/US2015/032485 Written Opinion dated Oct. 16, 2016.
[NPL634] PCT/US2016/030320 International Preliminary Report on Patentability, dated Apr. 20, 2017.
[NPL6] PCT/US2015/032492 Written Opinion dated Nov. 19, 2015.
[NPL2] PCT/US2015/032492 International Search Report dated Nov. 19, 2015.
[NPL584] Office Action in App. No. AU 2015280604 dated Apr. 8, 2016.
[NPL601] Wester et al., A regenerable postassium and phosphate sorbent system to enhance dialysis efficacy and device portability: an in vitro study Nephrol Dial Transplant (2013) 28: 2364-2371 Jul. 3, 2013.
[NPL494] John Wm Agar: Review: Understanding sorbent dialysis systems, Nephrology, vol. 15, No. 4, Jun. 1, 2010, pp. 406-411.
[NPL614] PCT/US2016/030304 International Search Report dated Jul. 27, 2016.
[NPL620] PCT/US2016/030320 Written Opinion dated Jul. 28, 2016.
[NPL626] PCT/US2015/032485 International Search Report and Written Opinion dated Oct. 16, 2015.
[NPL3] PCT/US2015/019901 International Search Report and Written Opinion dated Jun. 5, 2015.
PCT/US2016/030304_IPRP.
European Search Report for App. No. 15812081.6, dated Mar. 8, 2018.
PCT/US2015/032494 International Preliminary Report on Patentablity dated Dec. 27, 2016.
Office Action in Japanese Application No. 2016-553344, dated Apr. 24, 2018.

ZIRCONIUM PHOSPHATE AND ZIRCONIUM OXIDE RECHARGER CONTROL LOGIC AND OPERATIONAL PROCESS ALGORITHMS

FIELD OF THE INVENTION

The invention relates to control logic and processes for monitoring and controlling sorbent rechargers. The sorbent rechargers and related control logic and process algorithms monitor and test flow, temperature, conductivity, pressure, and volume, as well as the heaters and pumps, to ensure proper operation during recharging of zirconium phosphate, zirconium oxide, or both zirconium phosphate and zirconium oxide. In addition, the sorbent rechargers can perform periodic rinse cycles and check for appropriate chemical inputs for the recharging process using sensors as described herein.

BACKGROUND

Zirconium phosphate and zirconium oxide are used in sorbent dialysis to remove waste and unwanted solutes from spent dialysate. Generally, zirconium phosphate removes ammonium, potassium, calcium, and magnesium ions from dialysate while the zirconium oxide removes anions such as phosphate or fluoride ions. Both materials are usually packaged together in a cartridge of some type or packed in separate cartridges. Usually, sorbent cartridges are discarded and replaced after use. The discarded sorbent cartridges are broken down and the individual materials separated from each other. Because zirconium phosphate and zirconium oxide are expensive and rechargeable, sorbent re-processers treat the recovered zirconium phosphate and zirconium oxide with chemical solutions. The recycling process requires transporting the materials to reprocessing facilities and involves laborious recycling steps in addition to recharging the sorbent materials. Further, the sorbent material cannot be immediately reused, and must be added to a new sorbent cartridge and repackaged for sale. Safe disposal of the chemical waste from solutions used to recharge the materials may also require additional steps such as neutralizing the recharging solutions. Conventional methods drive up costs and infrastructure requirements, and increase complexity and waste.

Hence, there is a need for systems and methods capable of ensuring that the recharging is properly carried out. The need extends to systems and methods for testing the fluid lines, communication systems, pumps, valves, and chemicals used in the recharging process. The need includes appropriate control logic and process algorithms for monitoring, testing, cycling, and operating sorbent rechargers.

SUMMARY OF THE INVENTION

The first aspect of the invention is drawn to a recharger having a first receiving compartment for a first reusable sorbent module; the receiving compartment comprising a first sorbent module inlet and a first sorbent module outlet; a first inlet line fluidly connected to the first sorbent module inlet; a first effluent line fluidly connected to the first sorbent module outlet; at least one of an disinfectant source, a brine source, a base source, and a water source fluidly connected to the first inlet line; at least a first pump positioned in the first inlet line for pumping fluid from the disinfectant source, brine source, and water source to the first sorbent module inlet; at least one flow sensor, at least one pressure sensor, at least one temperature sensor, and at least one conductivity sensor; and a control system in communication with at least one of the flow sensor, pressure sensor, temperature sensor and conductivity sensor; the control system for controlling the first pump. In any embodiment, each of the features described as relating to a first receiving compartment can also relate to a second, third, fourth, or additional receiving compartments.

In any embodiment, the recharger can have a user interface in communication with the control system.

In any embodiment, the control system can be configured to determine whether at least one of the pressure, flow rate, temperature, and conductivity are within predetermined ranges.

In any embodiment, the control system can generate an alert indicating a leak when the pressure is below the predetermined range; and the control system can generate an alert indicating an occlusion alert when the pressure is above the predetermined range.

In any embodiment, at least one conductivity sensor is located upstream of the first sorbent module inlet; the control system can determine the flow rate and conductivity of a fluid upstream of the first sorbent module; the control system can generate an alert indicating a pump failure when the flow rate is below the predetermined range and the conductivity of a fluid upstream of the first sorbent module inlet is within a predetermined range; and the control system can generate an alert indicating a chemical run-out when the control system determines the flow rate is below the predetermined flow rate range and that the conductivity of the fluid upstream of the first sorbent module inlet is below the predetermined range.

In any embodiment, the recharger can have a heater and a heat exchanger in the first inlet line, the temperature sensor in communication with the control system; wherein the control system controls the heater based on data from the temperature sensor; wherein the control system generates an alert if the temperature in the first inlet line does not reach a predetermined temperature in a predetermined amount of time.

In any embodiment, the control system can generate an alert if the temperature in the first inlet line does not reach a predetermined temperature in a predetermined amount of time.

In any embodiment, the recharger can have a second temperature sensor in the first effluent line, wherein the control system generates an alert if the temperature in the first effluent line does not reach a predetermined temperature in a predetermined amount of time; and the control system can calculate an amount of brine necessary for recharging a sorbent module containing zirconium phosphate based, at least in part, on the temperature in the first effluent line.

In any embodiment, the recharger can have a second receiving compartment for a second reusable sorbent module; the second receiving compartment comprising a second sorbent module inlet and a second sorbent module outlet; a second inlet line fluidly connected to the second sorbent module inlet; a second effluent line fluidly connected to the second sorbent module outlet; wherein the disinfectant source, the base source, and the water source are fluidly connected to the second inlet line; at least a second pump positioned in the second inlet line for pumping fluid from the disinfectant source, base source, and water source to the second sorbent module inlet; at least one flow sensor, at least one pressure sensor, at least one temperature sensor, and at least one conductivity sensor positioned in the second inlet line; wherein the control system is in communication with the second pump, and at least one of the flow sensor, pressure sensor, temperature sensor, and conductivity sensor positioned in the second inlet line.

In any embodiment, at least one conductivity sensor can be positioned in the first effluent line; wherein the control system controls the at least one pump to pump fluid from the disinfectant source, brine source, and/or water source through the first reusable sorbent module; and wherein the control system determines a conductivity of fluid in the first effluent line based on data from the conductivity sensor positioned in the first effluent line; wherein at least one conductivity sensor is positioned in the second effluent line; wherein the control system controls the second pump to pump fluid from the disinfectant source, base source, and/or water source through the second reusable sorbent module; and wherein the control system determines a conductivity of fluid in the second effluent line based on data from the conductivity sensor positioned in the second effluent line.

In any embodiment, the second effluent line can be fluidly connected to the first effluent line at a junction; and the recharger can have a static mixer at or downstream of the junction. The control system can calculate a neutralization ratio based on the conductivity of the fluid in the first effluent line and the conductivity of the fluid in the second effluent line; and the control system can control the second pump and the first pump based on data from the conductivity sensor in the first effluent line and the conductivity sensor in the second effluent line; and the control system can control the first pump and second pump to generate a fluid with a within a predetermined pH range in the static mixer based on the neutralization ratio.

In any embodiment, the control system can calculate a neutralization ratio based on the conductivity of the fluid in the first effluent line and the conductivity of the fluid in the second effluent line; and wherein the control system controls the second pump and the first pump based on data from the conductivity sensor in the first effluent line and the conductivity sensor in the second effluent line; and the control system can control the first pump and second pump to generate a fluid with a within a predetermined pH range in the static mixer based on the neutralization ratio.

In any embodiment, the predetermined pH range can be between 5 and 9.

In any embodiment, the control system can control the first pump to convey fluid with an acidic pH through the first inlet line and control the second pump to convey fluid with a basic pH through the second inlet line concurrently.

In any embodiment, the control system can determine the flow rate, pressure, and conductivity of a fluid upstream of the first sorbent module at preset times.

In any embodiment, the control system can stop the second pump when the conductivity of the fluid in the second effluent line reaches a preset conductivity the control system can stop the first pump when the conductivity of the fluid in the first effluent line reaches a predetermined range.

In any embodiment, control system can stop the first pump when the conductivity of the fluid in the first effluent line reaches a preset conductivity.

In any embodiment, wherein the control system can start the first pump and second pump when the conductivity in the first effluent line reaches a preset conductivity.

In any embodiment, the control system can calculate an amount of brine necessary for recharging a zirconium phosphate module based, at least in part, on the temperature in the first effluent line.

In any embodiment, the control system can control the first pump to pump water from the water source through the first inlet line after pumping a first fluid through the first inlet line and before pumping a second fluid through the first inlet line.

In any embodiment, the sorbent recharger can include a heat exchanger; the heat exchanger fluidly connected to the first inlet line and first effluent line.

In any embodiment, the control system can determine an amount of base pumped through the first inlet line.

Any of the features disclosed as being part of the first aspect of the invention can be included in the invention, either alone or in combination.

The second aspect of the invention is drawn to a method including the steps of pumping fluid from a disinfectant source, a base source, a brine source, a water source, or combinations thereof through a recharging flow path to a first sorbent module; and determining a presence of a leak, occlusion, pump failure, chemical mismatch, or chemical run-out; wherein determining the presence of an occlusion includes determining that a pressure in the recharging flow path is above a predetermined range; wherein determining the presence of a pump failure includes the steps of determining that a flow rate in the recharging flow path is below a predetermined range and determining that a conductivity at a sorbent module inlet of the first sorbent module is within a predetermined range; and wherein determining the presence of a chemical run out includes the steps of determining that a flow rate in the recharging flow path is below a predetermined range and determining that a conductivity at a sorbent module inlet of the first sorbent module is below a predetermined range. In any embodiment, each of the features described as relating to a first sorbent module can also relate to a second, third, fourth, or additional sorbent module.

In any embodiment, determining the presence of a leak can include determining a pressure in the recharging flow path is below a predetermined range.

In any embodiment, determining the presence of an occlusion can include determining a pressure in the recharging flow path is above a predetermined range.

In any embodiment, determining a pump failure can include the steps of determining a flow rate in the recharging flow path is below a predetermined range; and determining a conductivity at a fluid inlet of the first sorbent module within a predetermined range.

In any embodiment, determining the presence of a chemical run-out can include the steps of determining a flow rate in the recharging flow path is below a predetermined range; and determining a conductivity at a fluid inlet of the first sorbent module is below a predetermined range.

In any embodiment, the method can include the steps of pumping fluid from an disinfectant source, a base source, a brine source, a water source, or combinations thereof through the recharging flow path to a second sorbent module; and pumping fluid through a first effluent line fluidly connected to the first sorbent module and a second effluent line fluidly connected to the second sorbent module to a static mixer or a common reservoir; determining a conductivity of a fluid in the first effluent line and determining and conductivity of a fluid in the second effluent line; and calculating a neutralization ratio based on a conductivity of fluid in the first effluent line and the second effluent line; wherein the step of pumping fluid from the first effluent line and the second effluent line to the static mixer or common reservoir includes controlling a flow rate of the fluid in the first effluent line and second effluent line based on the neutralization ratio to generate a fluid in the static mixer or common reservoir within a predetermined pH range.

In any embodiment, the method can include the steps of determining a conductivity of a fluid in the first effluent line and determining a conductivity of a fluid in the second effluent line; and calculating a neutralization ratio based on a conductivity of fluid in the first effluent line and the second effluent line; wherein the step of pumping fluid from the first effluent line and the second effluent line to the static mixer or common reservoir comprises controlling a flow rate of the fluid in the first effluent line and second effluent line based on the neutralization ratio to generate a fluid in the static mixer or common reservoir within a predetermined pH range.

In any embodiment, the first sorbent module can contain zirconium phosphate; and the fluid can contain a brine solution; and the method can include the steps of determining a temperature of the brine solution fluid in a first effluent line fluidly connected to the first sorbent module; and calculating an amount of brine necessary for recharging the zirconium phosphate based, at least in part, on the temperature in the first effluent line.

In any embodiment, the first sorbent module can contain zirconium oxide, and the method can include determining an amount of base pumped through the first sorbent module.

In any embodiment, the method can include pumping fluid from the disinfectant source into the first sorbent module; determining a conductivity in the first effluent line; and stopping pumping the fluid from the disinfectant source when the conductivity in the first effluent line is within a predetermined range.

In any embodiment, the method can include pumping water from the water source through into the first sorbent module at a predetermined time after stopping pumping fluid from the disinfectant source.

In any embodiment, the method can include venting the first sorbent module at a predetermined time after stopping pumping fluid from the disinfectant source.

In any embodiment, the method can include pumping fluid from the disinfectant source into the first sorbent module while venting the first sorbent module.

Any of the features disclosed as being part of the second aspect of the invention can be included in the invention, either alone or in combination.

DETAILED DESCRIPTION OF THE INVENTION

Figure 1:
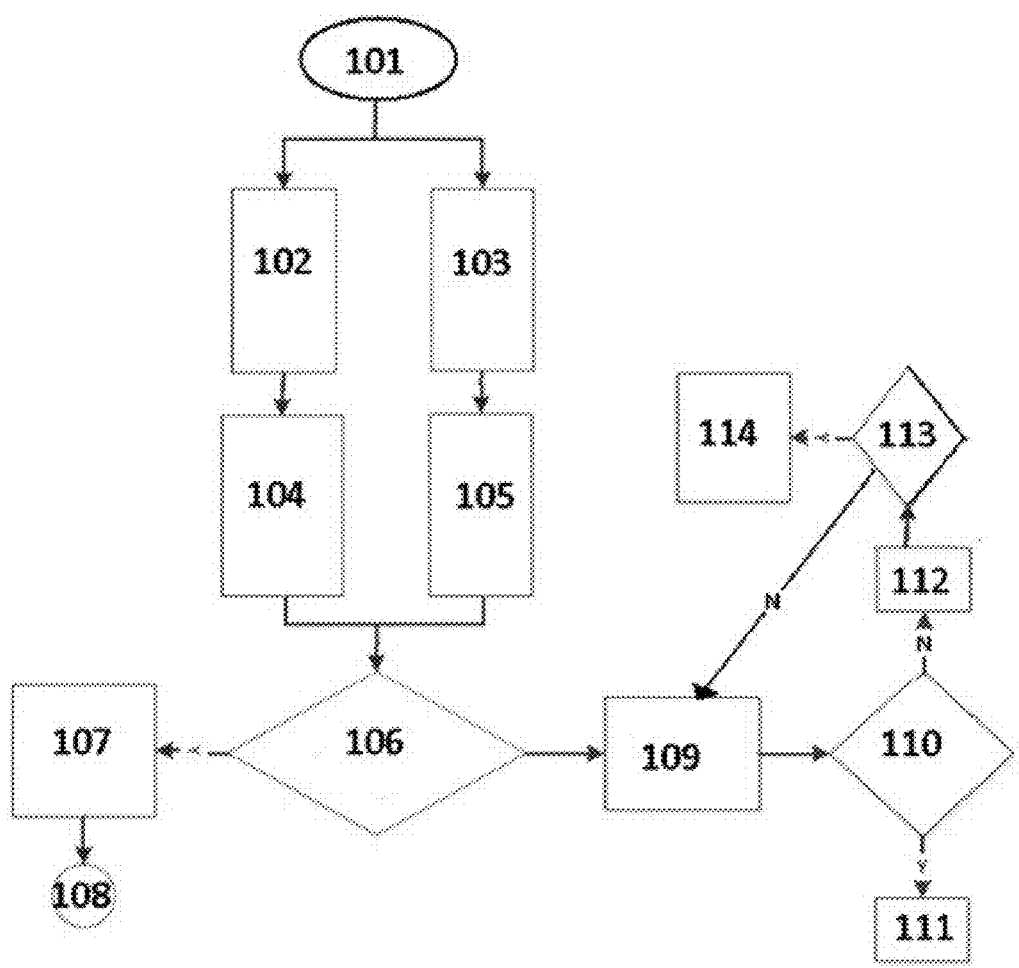
FIG. 1 illustrates operation process algorithms for conducting a recharger communication test.

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

The term "acidic pH" refers to an aqueous solution having a pH of less than 7.

An "alert" is any tactile, visual, or audio cue indicating the state of a system or component.

A "base source" is a fluid or concentrate source from which a basic solution can be obtained.

The term "basic pH" refers to an aqueous solution having a pH of greater than 7.

A "brine source" is a fluid or concentrate source from which a brine solution can be obtained. As used herein, a brine solution can refer to any solution comprising acids, bases and/or salts.

The terms "calculating a neutralization ratio" and to "calculate a neutralization ratio" refer to determining a relative amount of a first fluid necessary to neutralize a second fluid.

The terms "calculating an amount of brine necessary for recharging a sorbent module" or to "calculate an amount of brine necessary for recharging a sorbent module" refer to determining a volume of a brine solution that will result in recharging the sorbent module given a temperature, concentration, and flow rate of the brine solution.

The term chemical mismatch" refers to a state in which an incorrect fluid is present in a fluid source.

The term "chemical run-out" refers to a state in which one or more chemicals are no longer available to a system.

A "common reservoir" can be a container for collecting fluid of any type from one or more fluid sources including fluid lines or other reservoirs. The "common reservoir" can for example, store used or waste fluids.

The term "communication" refers to an electronic link between two components.

The term "comprising" includes, but is not limited to, whatever follows the word "comprising." Use of the term indicates the listed elements are required or mandatory but that other elements are optional and may be present.

The term "concurrently" refers to two processes or events taking place at the same time.

The term "conductivity" refers to the inverse of the resistance of a material or fluid A "conductivity sensor" is a sensor configured to measure the conductivity of a fluid.

The term "consisting of" includes and is limited to whatever follows the phrase "consisting of." The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The terms "contain," "containing," or "contained" as used herein means to keep a material within a specific place. "Contain" can refer to materials placed within a component, absorbed onto a component, bound to a component, or any other method of keeping the material in a specific place.

The term "control" or "controls" refers to the ability of one component to direct the actions of a second component.

A "control system" is any device which monitors and affects the operational conditions of a system. The operational conditions are typically referred to as output variables of the system wherein the output variables can be affected by adjusting certain input variables.

The terms "determining" and "determine" refer to ascertaining a particular state of a system or variable(s).

A "disinfectant source" is a fluid or concentrate source from which a disinfectant solution can be obtained. The disinfectant solution can be an acidic solution, such as a peracetic acid solution, or any other solution capable of disinfecting reusable sorbent modules.

The term "downstream" refers to a position of a first component in a flow path relative to a second component wherein fluid will pass by the second component prior to the first component during normal operation. The first component can be said to be "downstream" of the second component, while the second component is "upstream" of the first component.

An "effluent line" is a fluid passageway, tube, or path of any kind into which fluid exiting a container, module, or component will flow.

The term "flow rate" refers to a volume or quantity of liquid, gas, or a combination thereof, passing a particular point per unit time.

A "flow sensor" is a device capable of measuring an amount or rate of fluid, gas, or combination thereof, moving past or through a location.

A "fluid" is a liquid substance optionally having a combination of gas and liquid phases in the fluid. Notably, a liquid, as used herein, can therefore also have a mixture of gas and liquid phases of matter.

The term "fluidly connectable," "fluidly connect," "for fluid connection," and the like, refer to the ability of providing for the passage of fluid, gas, or combination thereof, from one point to another point. The two points can be within or between any one or more of compartments, modules, systems, components, and rechargers, all of any type. The connection can optionally be disconnected and then reconnected.

The terms "generates an alert" and to "generate an alert" refer to causing an alert to be created.

The terms "generates a fluid" and to "generate a fluid" refer to creating a fluid with a specified concentration, pH, temperature, and/or volume from one or more fluid sources.

A "heater" is a component capable of raising the temperature of a substance, container, or fluid.

The phrase "indicating a chemical-run out" refers to an alert that one or more chemicals are not available to the system.

The phrase "indicating a leak" refers to an alert that a leak potentially exists in the system.

The phrase "indicating an occlusion" refers to an alert that an occlusion potentially exists within a system.

The phrase "indicating a pump failure" refers to an alert that one or more pumps are not capable of pumping fluid at a desired flow rate.

An "inlet line" is a fluid line through which fluids can flow to enter a sorbent module.

A "junction" is a location where at least two fluid lines are connected to each other, with or without a valve.

The term "leak" refers to fluid exiting a fluid line or component at a location that the fluid is not intended to exit the fluid line or component.

The term "mixing" generally refers to causing one or more fluids from any source to combine together. For example, "mixing" can include turbulent flow at a location in a fluid line or a junction. Another example of "mixing" can include receiving one or more fluids in a component configured to receive fluids from one or multiple sources and to mix the fluids together in the component. Additionally, mixing can refer to the dissolution of a solid or solids with a fluid, wherein the solid or solids is dissolved in the fluid.

The term "neutralization ratio" refers to the relative amount of a first fluid necessary to neutralize a second fluid.

An "occlusion" is a blockage in a fluid line.

The term "positioned" or "position" refers to a physical location of a component or structure.

A "predetermined range" is a range of values for a variable that is calculated or determined prior to measuring the variable.

The term "preset" refers to particular time periods determined prior to a process.

The term "pressure sensor" refers to a device for measuring the pressure of a gas or liquid in a vessel, container, or fluid line.

The term "pump" refers to any device that causes the movement of fluids, gases, or combinations thereof, by applying suction or pressure.

The term "pump failure" refers to a state in which one or more pumps are not capable of pumping fluid at a desired flow rate.

The terms "pumping," "pumped," or to "pump" refer to moving a fluid, gas, or combination thereof, with a pump.

A "receiving compartment" is a space within a recharger into which a sorbent module to be recharged is placed.

A sorbent "recharger" is an apparatus designed to recharge at least one sorbent material.

"Recharging" refers to treating a sorbent material to restore the functional capacity of the sorbent material to put the sorbent material back into a condition for reuse or use in a new dialysis session. In some instances, the total mass, weight and/or amount of "rechargeable" sorbent materials remain the same. In some instances, the total mass, weight and/or amount of "rechargeable" sorbent materials change. Without being limited to any one theory of invention, the recharging process may involve exchanging ions bound to the sorbent material with different ions, which in some instances may increase or decrease the total mass of the system. However, the total amount of the sorbent material will in some instances be unchanged by the recharging process. Upon a sorbent material undergoing "recharging," the sorbent material can then be said to be "recharged." Recharging of rechargeable sorbent materials is not the same as replenishing of a sorbent material such as urease. Notably, urease is not "recharged," but can be replenished, as defined herein.

A "recharging flow path" is a path through which fluid can travel while recharging sorbent material in a reusable sorbent module.

The terms "sensing," "sensed" or to "sense" refer to determining one or more parameter or variable.

A "sensor" is a component capable of determining or sensing the states of one or more variables in a system.

A "sorbent cartridge module" or "sorbent module" means a discreet component of a sorbent cartridge. Multiple sorbent cartridge modules can be fitted together to form a sorbent cartridge of two, three, or more sorbent cartridge modules. In some embodiments, a single sorbent cartridge module can contain all of the necessary materials for dialysis. In such cases, the sorbent cartridge module can be a "sorbent cartridge."

A "sorbent module inlet" is a connector through which a fluid, slurry, or aqueous solution can enter a sorbent module.

A "sorbent module outlet" is a connector through which a fluid, slurry, or aqueous solution can exit a sorbent module.

The terms to "start a pump" or "starting a pump" refer to activating a pump to cause the pump to start pumping a fluid.

A "static mixer" is a component configured to receive fluids from one or multiple sources and to mix the fluids together. The static mixer may include components that agitate the fluids to further mixing.

The terms to "stop" a pump or "stopping a pump" refer to shutting off a pump to prevent the pump from pumping a fluid.

The term "temperature sensor" refers to a device for measuring the temperature of a gas or liquid in a vessel, container, or fluid line.

The term "upstream" refers to a position of a first component in a flow path relative to a second component wherein fluid will pass by the first component prior to the second component during normal operation. The first component can be said to be "upstream" of the second component, while the second component is "downstream" of the first component.

A "user interface" is a component that allows a user to communicate with a processor, computer, control system and the like. A user of the "user interface" can input information and can receive information from the processor or control system.

The term "venting" or "to vent" refers to opening one or more outlets in a container or module to allow fluid, gas, or a combination thereof, to escape.

A "water source" is a fluid source from which water can be obtained.

Recharger Control Algorithms

A recharger can be configured to recharge zirconium phosphate and zirconium oxide. To effectively and safely recharge the sorbent materials, operational process algorithms are needed in each step of the recharging process. FIG. 1 illustrates an operational process algorithm for ensuring proper communication between a recharger control system and zirconium phosphate and zirconium oxide recharging flow paths. The control system can be any component capable of monitoring and affecting the states of the recharger flow paths. The control system can use processors, memory and computer components to carry out the functions described. The control system is in communication with the pumps and valves of the recharger flow paths and can control the pumps and valves in accordance with stored instructions. The control system is also in communication with various sensors in the recharger flow paths. The control system receives data from the sensors and controls the pumps and valves of the recharger flow path on the basis of the data in accordance with stored instructions.

In step 101, the user starts the recharging process. A recharger control system sends a test message to a zirconium phosphate control system in step 102 and to a zirconium oxide control system in step 103. The zirconium phosphate control system sends a return message to the recharger control system in step 104, and the zirconium oxide control system sends a return message to the recharger control system in step 105. The zirconium phosphate and zirconium oxide control systems can also send test messages to each other. In step 106, the recharger control system determines whether each of the return messages has been received. If so, in step 107, the recharger control system sends messages to each of the zirconium phosphate and zirconium oxide control systems to begin the recharging process, indicated at step 108 in FIG. 1. If either of the return messages is not received by the recharger control system, the recharger control system generates an error message to the user indicating a communication failure. After the power up sequence is successful, the recharger control system communication link health is monitored by "Heartbeat Message." In step 109 a heartbeat message is sent to each of the zirconium phosphate and zirconium oxide control systems. The "heartbeat message" is a test message sent repeatedly at set intervals, such as once a second or once every 500 ms. One of skill in the art will understand that the interval between heartbeat messages can be set to any time. The recharger control system then checks to see if the heartbeat message was received in step 110. If the heartbeat message has not been received, a counter is increased in step 112. The recharger control system determines if the counter is above some pre-set threshold in step 113. If the counter is above the pre-set threshold, an error message is generated in step 114, indicating communication has been lost. If the counter is below the pre-set level, another heartbeat message is sent in step 109, until the heartbeat message is received or the counter exceeds the pre-set threshold. The pre-set threshold of the counter can be any number, including between 1 and 5 or greater. If the heartbeat message is received, the counter is reset in step 111 and the heartbeat message is sent again at set intervals.

Figure 2:
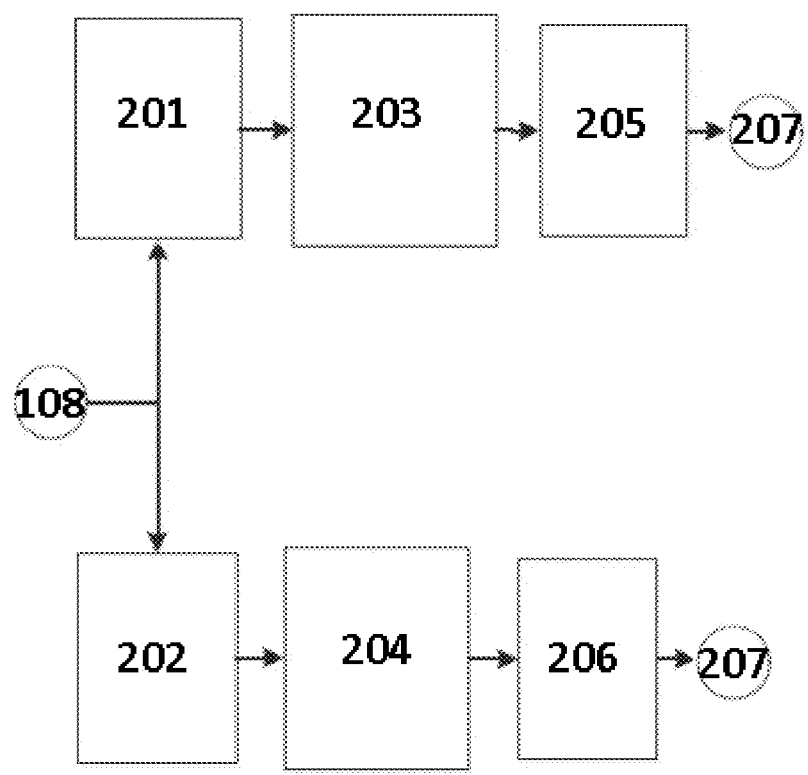
FIG. 2 illustrates operational process algorithms for beginning disinfection of sorbent modules with a recharger.

Once communication has been established between the recharger control system and each of the zirconium oxide, the recharging process can begin, as illustrated in FIG. 2, starting with step 108 of FIG. 1. The control system controls the pumps, valves, heaters and other components to generate and deliver the recharging fluids with the correct concentrations, flow rates, and temperature. The control system can communicate with the components of the recharging flow paths through any means known in the art, including WiFi, Bluetooth, or any other method. The control system sends instructions to the pumps, valves, heaters, or other components that cause these components to carry out the functions described. The recharger control system sends a message to the zirconium phosphate control system in step 201 and to the zirconium oxide control system in step 202 to begin a disinfection process. In step 203, the zirconium phosphate control system activates one or more pumps and valves within a zirconium phosphate recharging flow loop to begin filling the zirconium phosphate module with a disinfection solution from a disinfectant source. The disinfectant can be any disinfectant capable of disinfecting the sorbent modules and compatible with zirconium phosphate and zirconium oxide, including peracetic acid, bleach, or citric acid. In step 204, the zirconium oxide control system activates a different set of pumps and valves to begin filling the zirconium oxide control system with the disinfection solution. The disinfection solution is passed through the zirconium phosphate recharging flow path in step 205 and through the zirconium oxide recharging flow path in step 206. Each of the zirconium phosphate and zirconium oxide control systems can begin a chemical and system test procedure in step 207.

Figure 3:
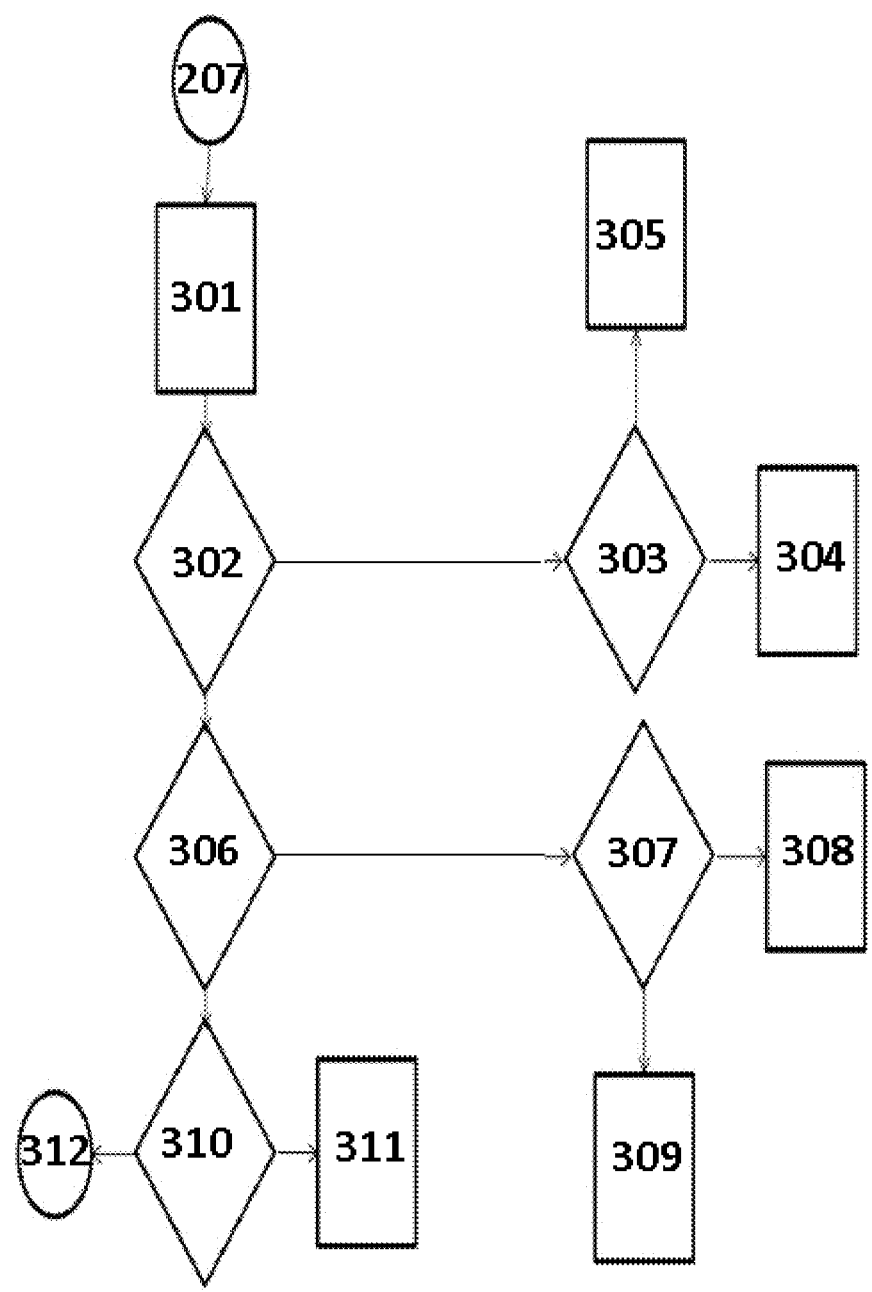
FIG. 3 illustrates operation process algorithms for conducting a chemical and system test.

As illustrated in FIG. 3, the chemical and system test procedure begins in step 207. In step 301, the system monitors the pressure in the fluid lines with one or more pressure sensors in communication with the control system. In step 302, the system determines whether the pressure as sensed by the pressure sensor is within a predetermined range. If the pressure is outside of the predetermined range, the system determines whether the pressure is above or below the predetermined range in step 303. If the pressure is below the predetermined range, the system generates an alert indicating a leak or rupture of a fluid line in step 304. If the pressure is above the predetermined range, the system generates an alert indicating an occlusion of the fluid lines in step 305. The predetermined range can be any range of pressures high enough to move fluid throughout the recharging flow paths but low enough to avoid damage to the lines and components. The lower range depends on the flow rate and is adjustable. The higher range is generally 2.0 bar, but can depend on the capabilities of the system. In any embodiment, the predetermined range can be between 1.0 and 2.0 Bar.

If the pressure is within the predetermined range, the system determines whether the flow rates of the fluid moving through the recharging flow paths are within a predetermined range with one or more flow sensors in communication with the control system in step 306. The predetermined range of flow rates can vary with the recharging process, as explained. In any embodiment, the predetermined range of the flow rates can be ±10% of the set flow rate. Alternatively, the predetermined range can be a flow rate deviation, such as ±20 mL/min of the set flow rate. If the sensed flow rates are outside of, or below, the predetermined range, the system determines the conductivity of the fluid at or upstream of the sorbent module inlets with a conductivity sensor in step 307. If the conductivity of the fluid is determined to be 0, or below a predetermined low range, the system generates an alert indicating a chemical run-out in step 308. If the conductivity of the fluid is greater than 0, or within a predetermined range, the system generates an error message indicating a pump failure in step 309.

If the fluid flow rates are determined to be within the predetermined range in step 306, the system determines whether the conductivity of the fluid at or upstream of the sorbent module inlets is within a predetermined range of an expected conductivity in step 310. The expected conductivity will vary depending on the particular solution being pumped through the recharging flow paths during the recharging process. In any embodiment, the predetermined range can be ±10% of the expected conductivity. If the conductivity is outside of the predetermined range, the system generates an alert indicating a possible chemical mismatch in step 311. If the conductivity is within the predetermined range, the system sends a message to the zirconium phosphate and zirconium oxide control systems to continue the recharging process in step 312. One of skill in the art will understand that the order of operations in chemical and system test procedure can be varied. For example, the system can determine whether the fluid flow rates are within a predetermined range prior to determining whether the pressure is within a predetermined range. Although shown as occurring at discrete times in the control algorithms, one of skill in the art will understand that the chemical and system test illustrated in FIG. 3 can be conducted at any time during the recharging process, including at preset times.

To avoid occlusion of the valves due to sodium precipitation, the control system can automatically cause the recharger to periodically rinse the system with water at preset times. The control system can also cause the recharger to rinse the system with water between chemicals. After pumping a first fluid, such as a disinfectant, through the recharging flow path, the control system can pump water through the recharging flow path to rinse the recharging flow path before pumping brine or base. The control system can cause the recharger to rinse the system any time the chemicals are changed.

The pressure, flow rate, and conductivity of the fluid are determined with various sensors located in the recharging flow paths, each of which is in communication with the control system. The sensors transmit data to the control system for determination of the system state. Based on the data received from the sensors, the control system determines whether the pressure, flow rate, and conductivity are within predetermined ranges by comparing the measured parameters from the sensors with predetermined ranges stored by the control system. The described alerts indicating a leak, an occlusion, a pump failure, or a chemical-run out can be generated by the system in any fashion, including through an audio or visual alert, or combinations thereof. The system can generate an audio alert by activating an alarm or tone informing a user that a leak, occlusion, pump failure, or chemical run-out has occurred or is occurring. The system can generate a visual alert by activating a warning light or creating a text based message on a user interface.

Figure 4:
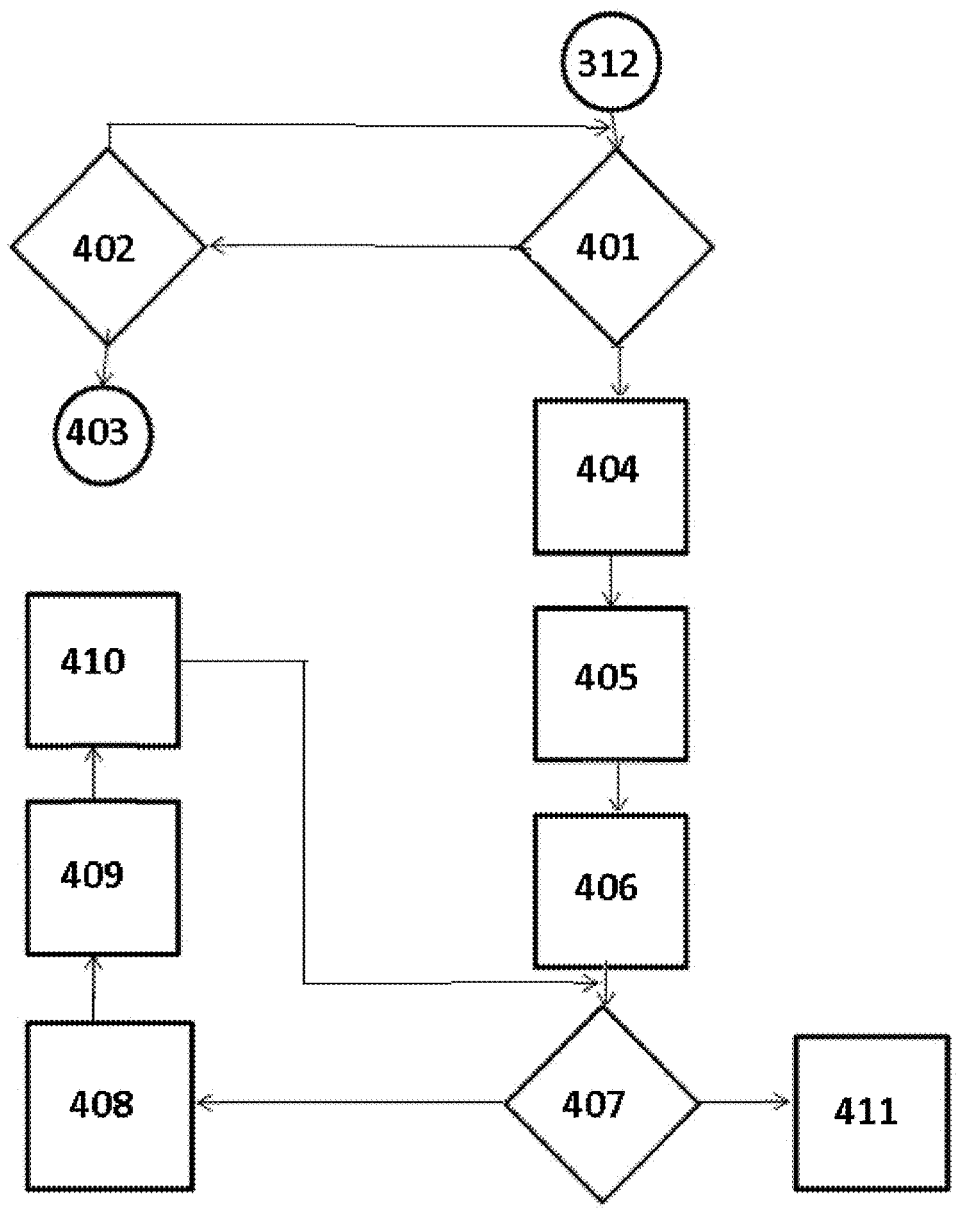
FIG. 4 illustrates control algorithms for disinfecting sorbent modules with a recharger.

FIG. 4 illustrates the control algorithms used during the disinfection process. After receiving instructions to continue the recharging process in step 312, the system begins to monitor the zirconium phosphate and zirconium oxide effluent line conductivity in step 401. Once the disinfectant has completely filled the sorbent modules the conductivity of the effluent should approach the conductivity of the disinfectant solution used for disinfection. If the conductivity is outside of some predetermined range of the expected conductivity, the system determines how much time has elapsed from the beginning of the disinfection process in step 402. If the time elapsed exceeds a predetermined threshold, the system can stop the recharging process in step 403 by stopping the pumps. The predetermined threshold is a range of time based on the amount of time expected to elapse before the sorbent module is completely filled with disinfectant. The expected amount of time varies with the size of the sorbent module and the disinfectant solution flow rate, and as such, the predetermined threshold can also vary. Because the zirconium phosphate sorbent module is generally larger than the zirconium oxide sorbent module, the predetermined threshold is higher for the zirconium phosphate recharging flow path than the zirconium oxide recharging flow path. If the predetermined threshold has not been reached, the system can continue to monitor the effluent conductivity in step 401.

As described, the disinfectant can be sequestered within the sorbent modules to ensure complete disinfection. Once the system determines the effluent conductivity is within a predetermined range of the disinfectant solution conductivity, the pump is stopped and valves closed in step 404 to sequester the disinfectant in the sorbent module. In step 405 the zirconium phosphate and zirconium oxide control systems send a message to the user interface system, and optionally displayed to the user, indicating the disinfection process has begun. In step 406, a timer is started to track the amount of time the disinfectant is sequestered within the sorbent module. The recharging control system tracks the time elapsed and determines if the disinfection process is complete in step 407. The disinfectant can be sequestered in the sorbent module for any length of time sufficient to disinfect the sorbent module, including between 5 and 20 minutes. Other suitable times are contemplated by the invention. Once the timer reaches the sequester time, the system can send a message indicating the disinfection process is complete in step 411.

As described, the disinfectant solution used for disinfection can be a peracetic acid solution. During disinfection, the peracetic acid solution may generate carbon dioxide, which needs to be vented from the sorbent modules. The carbon dioxide is vented at set periods of time to prevent the buildup of excess pressure. In step 407, the system determines whether the set period of time has elapsed, indicating the carbon dioxide should be vented. If the set period of time has elapsed, the system opens the valves and starts the pumps to vent the modules in step 408. In step 409, the disinfectant solution is pumped through the module for a set length of time to ensure venting of the carbon dioxide. The pump is shut off and the valves closed in step 410, and the system continues to monitor the timer in step 407.

Figure 5:
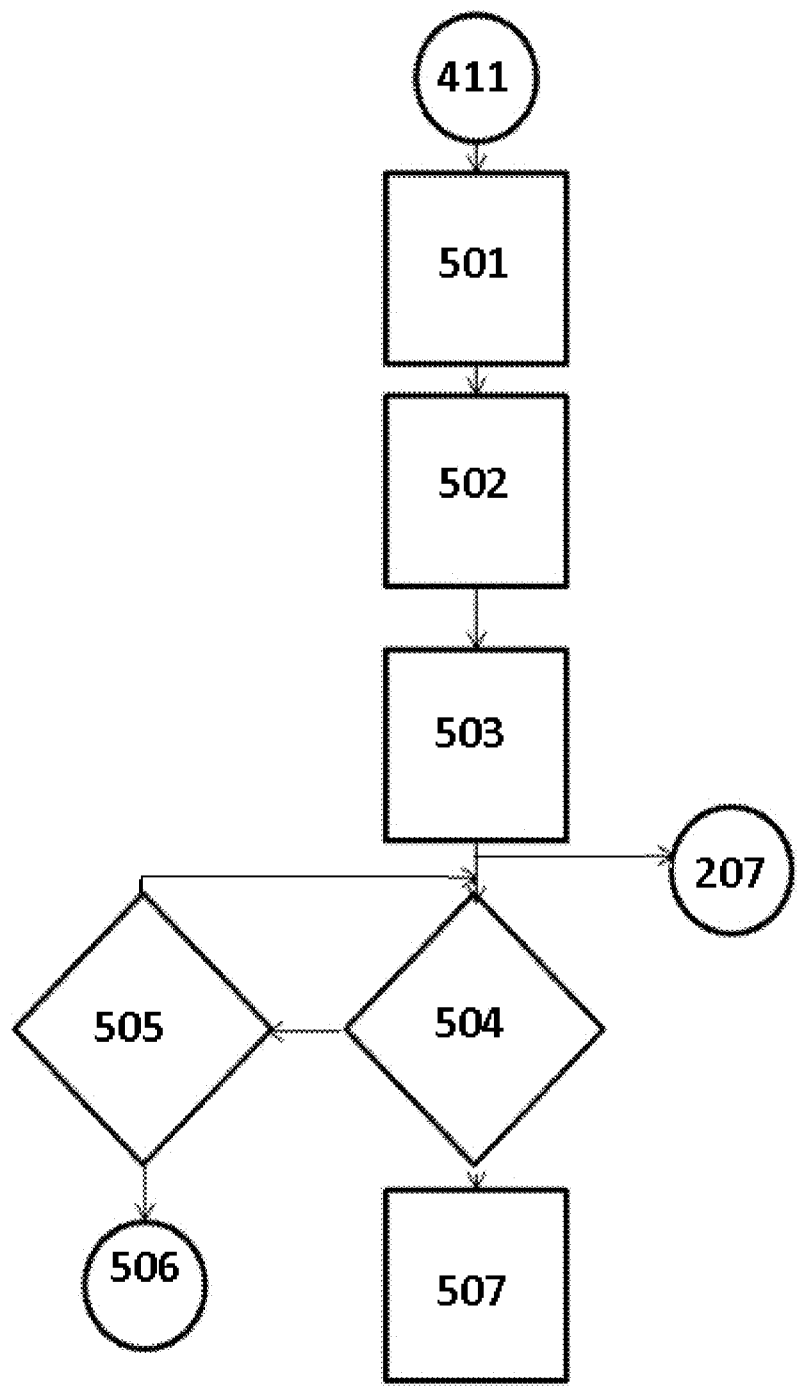
FIG. 5 illustrates control algorithms for rinsing sorbent modules after disinfection.

FIG. 5 illustrates the control algorithms for rinsing the modules after disinfection. After the system indicates that the disinfection of the zirconium phosphate and zirconium oxide modules are complete in step 411, the control system begins the rinse sequence in step 501. In step 502, the recharger flow paths are configured to pump water from a water source through the reusable modules. The water is pumped through the recharging flow paths in step 503. Concurrently, the control system conducts the chemical and system test sequence 207, as illustrated in FIG. 3. After conducting the chemical and system tests, the control system monitors the conductivity of the effluent of the zirconium phosphate and zirconium oxide modules in step 504 and determines whether the conductivity is within a pre-set range of the expected effluent conductivity. After the rinsing sequence is complete, the conductivity of the effluent should approach that of water. If the conductivity is not within a predetermined range of the expected conductivity, the system determines the time elapsed from the beginning of the rinse sequence in step 505. If the time elapsed exceeds a predetermined threshold, the system stops the recharging process in step 506 by stopping the pumps. The predetermined threshold is a range of time based on the amount of time expected to elapse before the sorbent module is completely rinsed of disinfectant. The expected amount of time varies with the size of the sorbent module and the water flow rate, and the predetermined threshold can also vary. Because the zirconium phosphate sorbent module is generally larger than the zirconium oxide sorbent module, the predetermined threshold is higher for the zirconium phosphate recharging flow path than the zirconium oxide recharging flow path. If the predetermined threshold has not been reached, the system continues to monitor the effluent conductivity in step 504. Once the system determines that the conductivity of the effluent is within the predetermined range, the system generates a message indicating the rinse process is complete in step 507.

Figure 6:
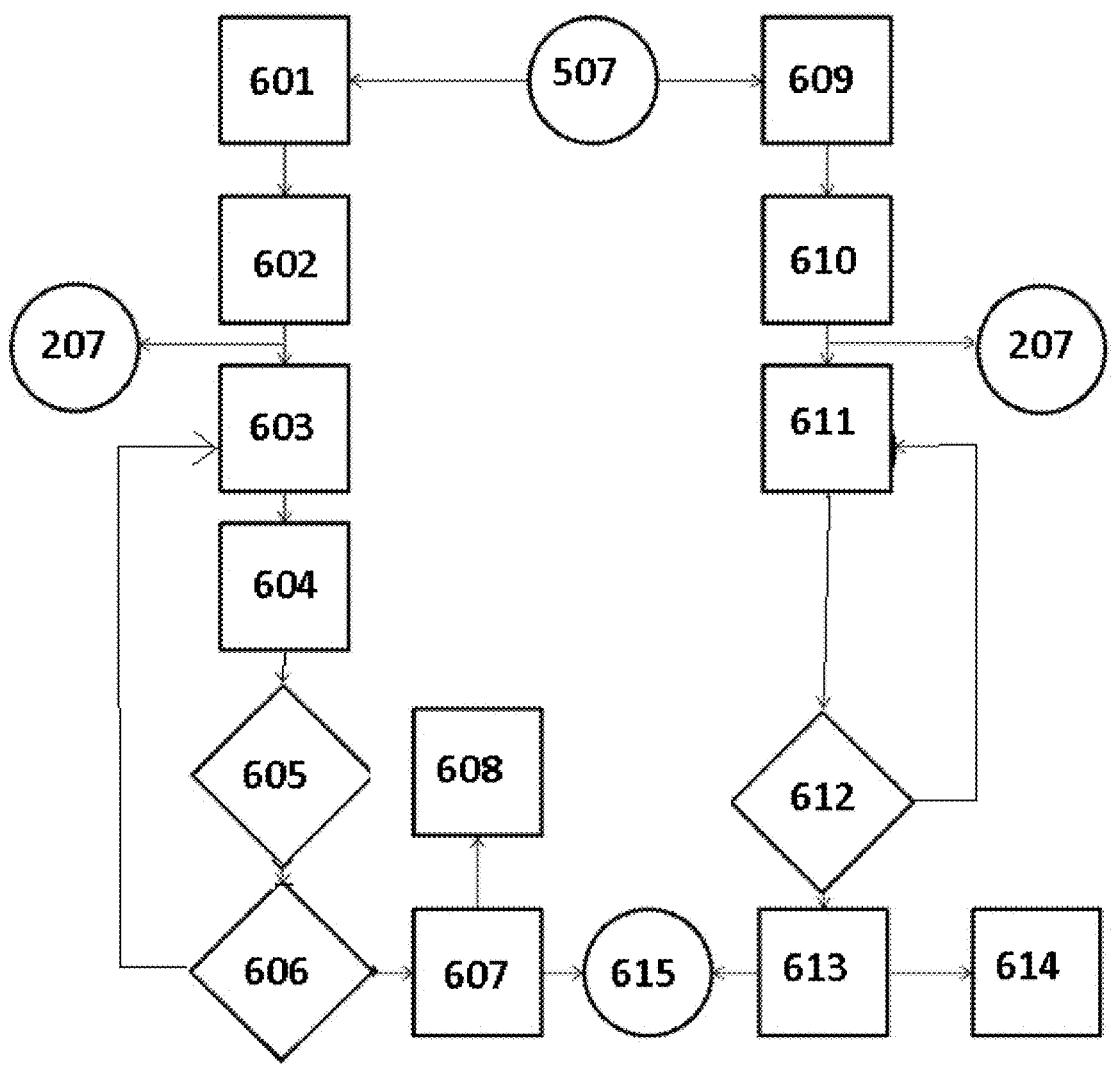
FIG. 6 illustrates control algorithms for a first stage of the recharging process.

After generating messages that the rinse process is complete in step 507, the system begins the first stage of the recharging process as illustrated in FIG. 6. The control system sends a message to the zirconium phosphate control system to begin the recharging process in step 601. As described, recharging of zirconium phosphate requires the use of a brine solution. During zirconium phosphate recharging, potassium, calcium, magnesium, and ammonium ions bound to the zirconium phosphate must be replaced by hydrogen and sodium ions. The final ratio of hydrogen to sodium ions on the recharged zirconium phosphate is determined by the pH, buffer capacity, and sodium concentration of the brine solution used in the recharging process. The brine solution can be a mixture of sodium chloride, sodium acetate, and acetic acid. In one non-limiting brine solution, the sodium chloride concentration can be between 2.5 M and 4.9 M, the sodium acetate concentration can be between 0.3 M and 1.1 M, and acetic acid concentration can be between 0.2 M and 0.8 M. The zirconium phosphate control system begins to pump brine solution from a brine source through the zirconium phosphate recharging flow path in step 602. As the system pumps brine solution through the zirconium phosphate module, the system performs a chemical and system check in step 207, as illustrated in FIG. 3. In step 603, the system continues to pump brine solution through the zirconium phosphate recharging flow path and calculates the volume of brine solution pumped into the zirconium phosphate module. In step 604, a heater can be operated to heat the brine solution, as recharging of zirconium phosphate can become more efficient at elevated temperatures. In step 605, the system determines the temperature of the brine solution entering the zirconium phosphate module to ensure the brine solution is heated to the proper temperature. In step 606, the system begins monitoring the conductivity of the effluent of the zirconium phosphate module with a conductivity sensor to determine when brine solution begins to exit the zirconium phosphate module. If the conductivity does not show brine present in the effluent, the system continues to pump brine through the zirconium phosphate flow path in step 603. Once brine is detected in the zirconium phosphate effluent, the system stops calculating the amount of brine pumped in step 607. A message is sent to the control system indicating the first stage of the zirconium phosphate recharging process is complete, as well as the total amount of brine pumped through the zirconium phosphate, in step 615. At the same time, the zirconium phosphate control system enters a wait state in step 608, wherein the pumps are stopped until the system indicates that the first stage of the zirconium oxide recharging process is complete.

Concurrently with the zirconium phosphate recharging, the system also sends a message to the zirconium oxide control system to begin the recharging process in step 609. As described, recharging of zirconium oxide requires the use of a base solution. The solution can be any suitable basic solution capable of replacing phosphate and other anions bound to the zirconium oxide with hydroxide ions. The hydroxide base can be any suitable base such as sodium hydroxide. One non-limiting example is sodium hydroxide having a concentration between 0.8 M and 1.2 M. In step 610, the base solution is pumped from a base source through the zirconium oxide recharging flow path to the zirconium oxide module. The system performs a chemical and system test in step 207, as illustrated in FIG. 3. In step 611, the system continues to pump the base solution through the zirconium oxide recharging flow path, and calculates the amount of base solution pumped. In step 612, the system monitors the conductivity of the zirconium oxide effluent and determines whether the effluent contains any base. If the system cannot detect the base solution, the system continues to pump the base solution through the zirconium oxide recharging flow path in step 611. Once base is detected in the zirconium oxide effluent, the system stops calculating the amount of base solution pumped in step 613. A message is sent to the control system indicating the first stage of the zirconium oxide recharging process is complete, as well as the total amount of base pumped through the zirconium oxide, in step 615. At the same time, the zirconium oxide control system enters a wait state in step 614, wherein the pumps are stopped until the system indicates that the first stage of the zirconium phosphate recharging process is complete.

The zirconium phosphate requires an acidic brine solution for recharging, while the zirconium oxide requires a basic solution. The dual recharging system described herein allows for inline neutralization of the zirconium phosphate effluent having an acidic pH with the zirconium oxide effluent having a basic pH. The first stage of recharging each module is halted as illustrated in FIG. 6, to ensure that the processes for inline neutralization are synchronized in each recharging flow path. One of skill in the art will understand that if inline neutralization is not required, the system does not need to synchronize the zirconium phosphate and zirconium oxide recharging processes, and the system need not enter a wait state as illustrated in FIG. 6.

Figure 7:
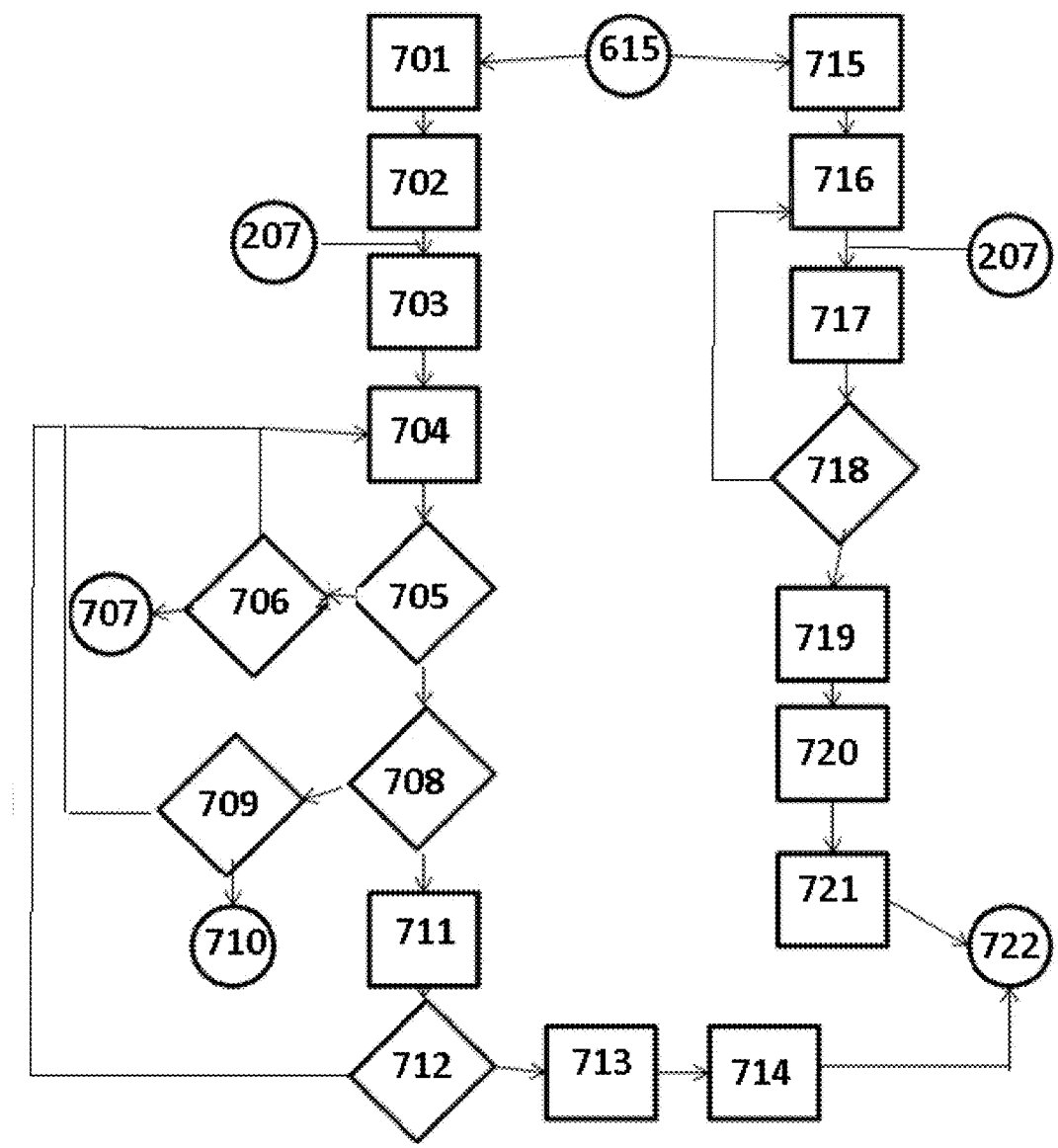
FIG. 7 illustrates control algorithms for a second stage of the recharging process.

After receiving the messages that the first stage of recharging is complete in step 615, the system can begin the second stage of the recharging process as illustrated in FIG. 7. In step 701 the control system sends a message to the zirconium phosphate control system to begin the second stage of the recharging process. The zirconium phosphate recharging flow path is configured to pump brine through the zirconium phosphate module in step 702. After the system begins to pump brine through the zirconium phosphate recharging flow path, the system performs a chemical and system test in step 207, as illustrated in FIG. 3. In step 703, the system begins to calculate the amount of brine solution pumped through the zirconium phosphate recharging flow path. In step 704, the heater is activated to heat the brine solution. In step 705, the system determines whether the temperature of the brine solution at the inlet of the zirconium phosphate module is above some pre-set temperature with a temperature sensor in communication with the control system. The pre-set temperature can be any elevated temperature, including between 65° C. and 95° C. If the brine solution has not reached the desired temperature, the system determines the length of time that has elapsed since the heater was activated in step 706. If the length of time is above some preset time period, the system can be stopped in step 707, and an alert generated indicating a possible heater failure. If the preset time has not been reached, the system continues to pump brine solution. In step 708, the system determines whether the temperature at the zirconium phosphate sorbent module outlet is above some preset temperature, generally lower than the inlet preset temperature. The pre-set temperature for the zirconium phosphate sorbent module outlet can be any elevated temperature, including between 60° C. and 80° C. If the zirconium phosphate effluent has not reached the preset temperature, the system determines the length of time that has elapsed since the heater was activated in step 709. If the length of time is above some preset time period, the system can be stopped in step 710, and an alert generated indicating a possible heater failure. If the preset time has not been reached, the system continues to pump brine solution. In step 711, the system calculates the amount of brine necessary for recharging the zirconium phosphate module to ensure complete recharging at the temperature measured at the zirconium phosphate sorbent module outlet. Because zirconium phosphate recharging is more efficient at higher temperatures, the amount of brine necessary for recharging the zirconium phosphate module varies with the temperature. The control system can calculate the amount of brine necessary for recharging the zirconium phosphate module through mathematical algorithms providing a relationship between temperature and the amount of brine necessary for recharging. Alternatively, the control system can use a look-up table populated with previous results for recharging at various temperatures. The control system can determine the temperature at the outlet of the zirconium phosphate module, and find an amount of brine necessary for recharging the zirconium phosphate module in the look-up table. In step 712, the system determines the total amount of brine pumped using a flow sensor in communication with the control system, and determines whether the total amount of brine is at least the calculated amount. If the total amount of brine pumped is less than the calculated amount, the system continues to pump brine. Once the total amount of brine pumped is at least the calculated amount, the control system determines whether the second stage of the zirconium oxide recharging process has been complete. Once the second stage of the zirconium oxide recharging process is complete, the zirconium phosphate recharging flow path is placed into a wait state in step 713 and the pumps and heater are stopped. If the second stage of the zirconium oxide recharging process is not complete, the control system will continue to pump brine through the zirconium phosphate. The total amount of brine pumped through the zirconium phosphate module is sent to the control system in step 714, and a message is generated indicating the second stage of recharging is complete in step 722.

In step 715, the control system sends a message to the zirconium oxide control system to begin the second stage of the recharging process. The zirconium oxide recharging flow path is configured to pump a base solution through the zirconium oxide module in step 716. After the system begins to pump the base solution through the zirconium oxide recharging flow path, the system performs a chemical and system test in step 207, as illustrated in FIG. 3. In step 717, the system begins calculating the total amount of base solution pumped through the zirconium oxide module. As described, the control system can calculate a neutralization ratio based on the brine solution and the base solution, wherein the neutralization ratio is the ratio of base solution to brine solution necessary for complete neutralization of each solution. The control system can calculate the neutralization ratio based on the known pH of the brine and base solutions. In step 718, the system, using the neutralization ratio, determines whether the amount of base solution pumped through the zirconium oxide module is the proper amount for neutralization of the brine solution pumped through the zirconium phosphate module to generate a fluid within a predetermined pH range safe for disposal. In any embodiment, the predetermined pH range can be between 5 and 9. If additional base solution is necessary for neutralization of the brine solution, the system continues to pump base solution through the zirconium oxide recharging flow path in step 716. The volume of base passed through the zirconium oxide recharging flow path in the second stage should be greater than or equal to the volume of base required to recharge the zirconium oxide, minus the total amount of brine pumped in the first stage of the zirconium phosphate recharging process, divided by the neutralization ratio, minus the total amount base pumped in the first stage of the zirconium oxide recharging process. Once enough base solution has been pumped through the zirconium oxide module to neutralize the brine solution pumped through the zirconium phosphate module, the control system determines whether the second stage of the zirconium phosphate recharging process is complete. If the second stage to the zirconium phosphate recharging process is complete, the system enters a wait state in step 719, and the pumps deactivated in step 720. If the second stage of the zirconium phosphate recharging process is incomplete, the system continues to pump base through the zirconium oxide. In step 721, the total amount of base solution pumped is sent to the control system. In step 722, a message is generated indicating the second stage of recharging is complete.

Figure 8:
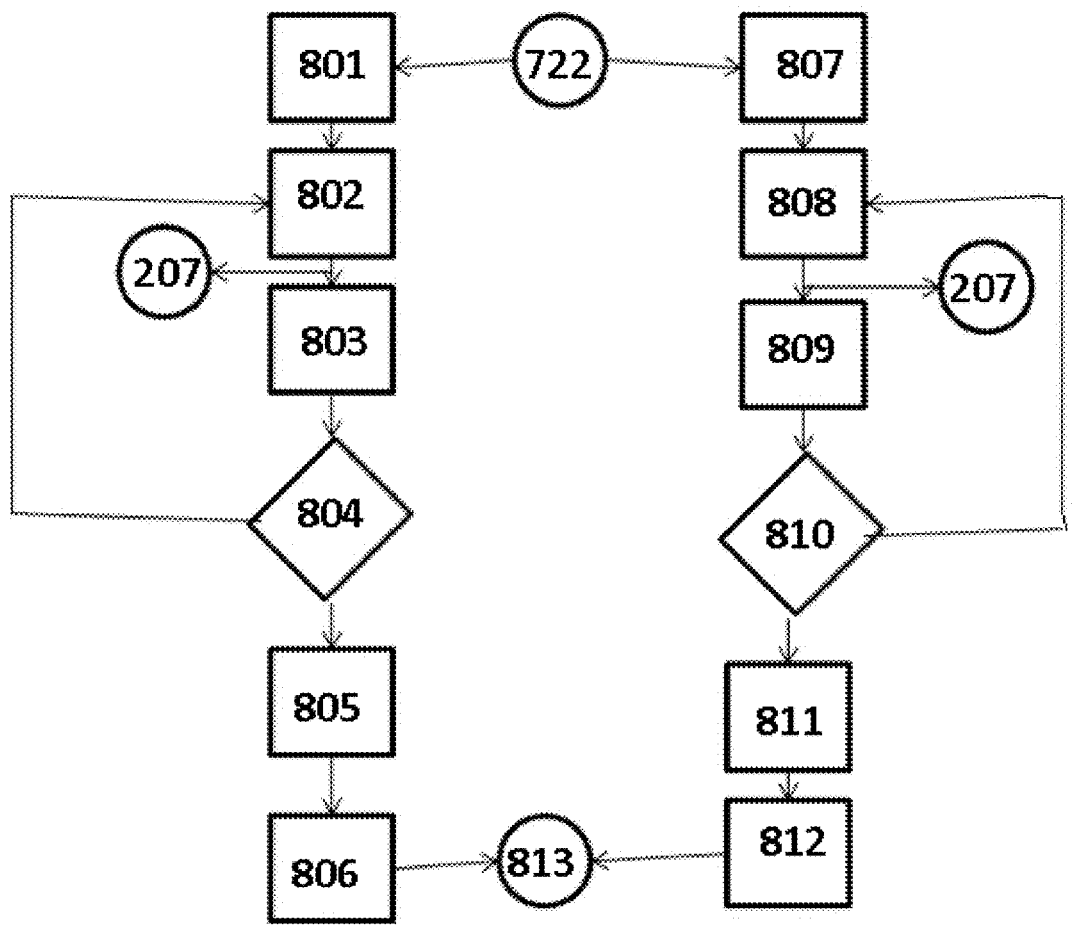
FIG. 8 illustrates control algorithms for a first stage of a rinse process.
Figure 9:
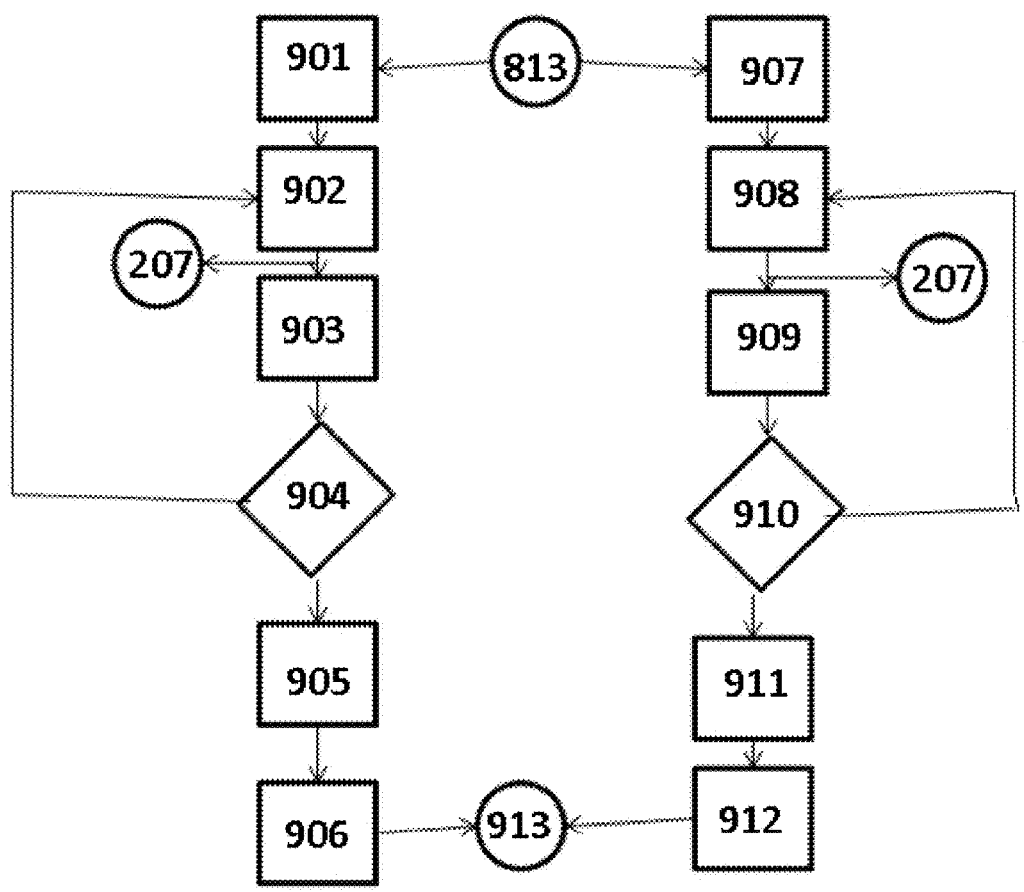
FIG. 9 illustrates control algorithms for a second stage of the rinse process.

After recharging the zirconium phosphate as illustrated in FIGS. 6-7, the system rinses the zirconium phosphate module to remove any remaining brine solution. FIG. 8 illustrates the control algorithms used in the first stage of the rinse process. After receiving the messages that the second stage of recharging is complete in step 722, the control system sends a message to the zirconium phosphate control system to begin the rinse process in step 801. In step 802, the zirconium phosphate recharging flow path is configured to pump water through the zirconium phosphate module. After the system begins to pump water, a chemical and system test is conducted in step 207, as illustrated in FIG. 3. In step 803, the volume of water pumped through the zirconium phosphate module is calculated with a flow sensor in communication with the control system at the zirconium phosphate sorbent module outlet. In step 804, the system determines whether the total amount of water pumped through the zirconium phosphate module is equal to the total amount of brine pumped in the first stage of the recharging process, minus the total amount of base pumped in the first stage of the recharging process times the neutralization ratio. If the volume of water pumped is less than the calculated volume, the system continues to pump water in step 802. Once the volume of water pumped reaches the calculated volume, the system enters a wait state in step 805, and the total amount of water pumped is transmitted to the recharger control system in step 806. The zirconium phosphate recharging control system generates a message indicating the first stage of rinsing is complete in step 813.

In step 807, the control system sends a message to the zirconium oxide control system to begin the third stage of the zirconium oxide recharging process. In step 808, the zirconium oxide recharging flow path is configured to pump base solution through the zirconium oxide recharging flow path. Base is pumped through the zirconium oxide recharging flow path in step 808 while the first stage of the zirconium phosphate rinse process begins to ensure neutralization of the brine solution in the zirconium phosphate effluent during the rinse process. The system conducts a chemical and system test in step 207, as illustrated in FIG. 3. In step 809, the volume of base solution pumped through the zirconium oxide module is calculated with a flow sensor in communication with the control system positioned at the zirconium oxide sorbent module outlet. In step 810, the system determines whether the volume of base solution pumped is equal to the volume of brine solution pumped in the first stage of the recharging process divided by the neutralization ratio, minus the volume of base pumped in the first stage of the recharging process. If the volume of base pumped in the third stage of the recharging process is less than this calculated volume, the system continues to pump base solution in step 808. Once the volume of base pumped in the third stage of the recharging process reaches the calculated volume, the system enters a wait state in step 811, and the total volume of base pumped is sent to the control system in step 812. A message indicating the third stage of the recharging process is complete is generated in step 813.

After receiving the messages that the first stage of the zirconium phosphate rinse process, and the third stage of the zirconium oxide recharging process are complete in step 813, the control system sends a message to the zirconium phosphate control system to begin the second stage of the rinse process in step 901. In step 902, the zirconium phosphate recharging flow path is configured to pump water through the zirconium phosphate module. After the system begins to pump water, a chemical and system test is conducted in step 207, as illustrated in FIG. 3. In step 903, the volume of water pumped through the zirconium phosphate module in the second stage of the rinse process is calculated. In step 904, the system determines whether the total amount of water pumped through the zirconium phosphate module in the second stage of the rinse process is equal to the total amount of base pumped in the first stage of the recharging process times the neutralization ratio. If the volume of water pumped is less than the calculated volume, the system continues to pump water in step 902. Once the volume of water pumped reaches the calculated volume, the system enters a wait state in step 905, and the total amount of water pumped is transmitted to the recharger control system in step 906. The zirconium phosphate recharging control system generates a message indicating the second stage of rinsing is complete in step 913.

In step 907, the control system sends a message to the zirconium oxide control system to begin the rinse process. In step 908, the zirconium oxide recharging flow path is configured to pump water through the zirconium oxide recharging flow path. The system conducts a chemical and system test in step 207, as illustrated in FIG. 3. In step 909, the volume of water pumped through the zirconium oxide module is calculated with a flow sensor in communication with the control system positioned at the zirconium oxide sorbent module outlet. In step 910, the system determines whether the volume of water pumped is equal to the volume of base solution pumped in the first stage of the recharging process. If the volume of water pumped in the rinse process is less than this calculated volume, the system continues to pump water in step 908. Once the volume of water pumped in the rinse process reaches the calculated volume, the system enters a wait state in step 911, and the total volume of water pumped is sent to the control system in step 912. A message indicating the second stage of the rinse process is complete is generated in step 913.

Figure 10:
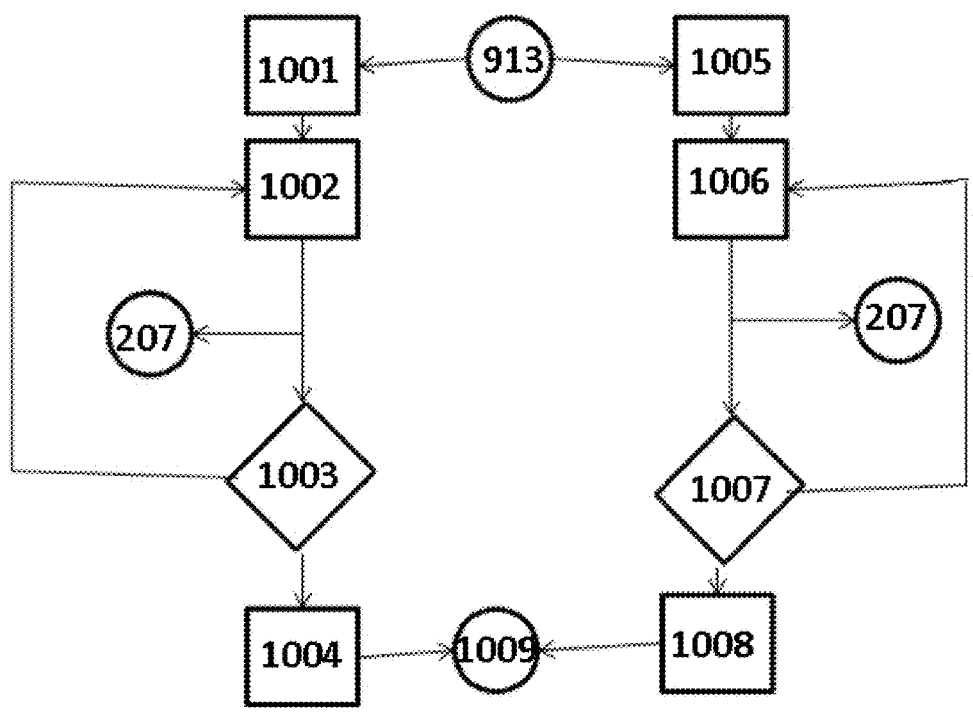
FIG. 10 illustrates control algorithms for a third stage of the rinse process.

FIG. 10 illustrates the third stage of the rinse process. After receiving the messages the second stage of the rinse process is complete in step 913, the recharger control system sends a message to the zirconium phosphate control system to begin the third stage of the rinse process in step 1001. The zirconium phosphate recharging flow path is configured to pump water through the zirconium phosphate module in step 1002. After starting a pump to pump water, the system performs a chemical and system check in step 207, as illustrated in FIG. 3. In step 1003, the conductivity of the zirconium phosphate effluent is measured with a conductivity sensor in communication with the control system. If the conductivity is outside of a predetermined range, the system continues to pump water in step 1002. The predetermined range can be the conductivity of water at the same temperature as the zirconium phosphate effluent, such as at 40° C., indicating the brine solution has been completely rinsed from the module. Once the system determines that the brine has been completely rinsed, the zirconium phosphate control system enters a wait state in step 1004, and a message is sent to the recharging control system that the rinse process is complete in step 1009.

In step 1005, the recharger control system sends a message to the zirconium oxide control system to begin the second stage of the rinse process. In step 1006 the zirconium oxide recharging flow path is configured to pump water through the zirconium oxide module. After starting a pump to pump water, the system performs a chemical and system check in step 207, as illustrated in FIG. 3. In step 1007, the conductivity of the zirconium oxide effluent is measured with a conductivity sensor in communication with the control system. If the conductivity is outside of a predetermined range, indicating some base solution remains in the effluent, the system continues to pump water in step 1006. Once the system determines that the base solution has been completely rinsed, the zirconium oxide control system enters a wait state in step 1008, and a message is sent to the recharging control system that the rinse process is complete in step 1009. After the control system receives both messages in step 1009, the recharging process is complete and the zirconium phosphate and zirconium oxide modules can be reused in dialysis.

Figure 11A:
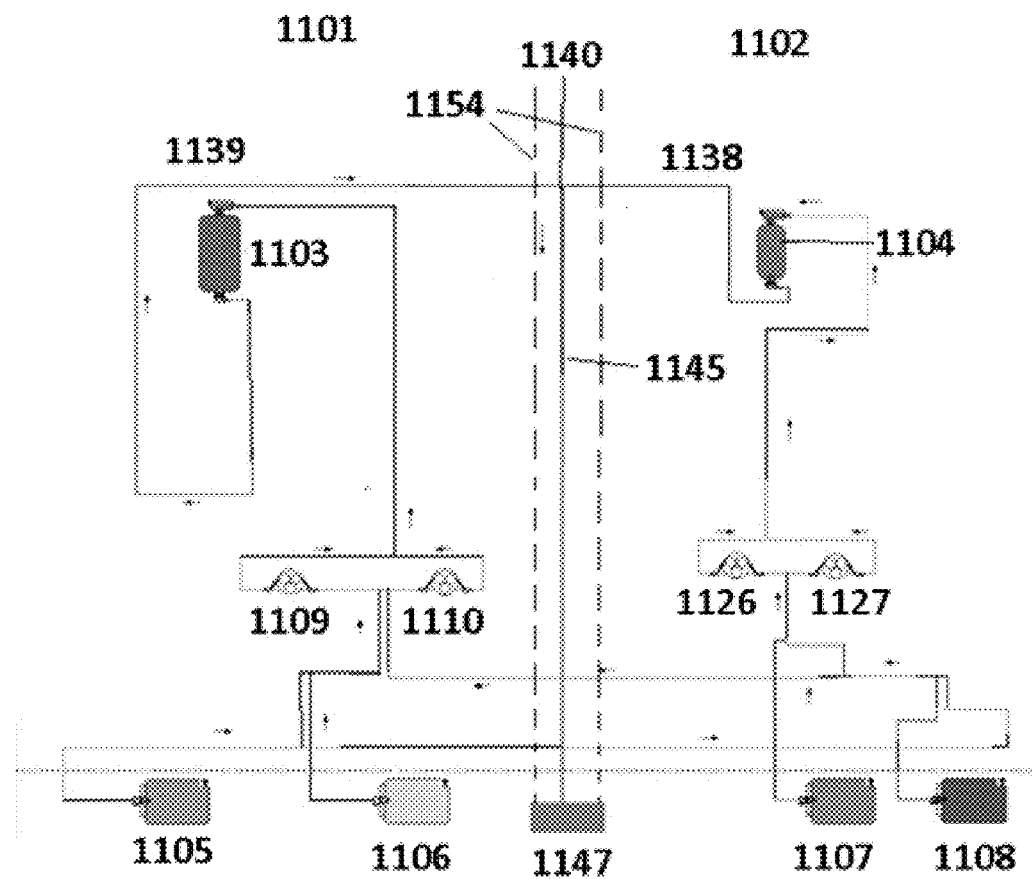
FIG. 11A shows a recharging flow path for recharging zirconium phosphate and zirconium oxide.
Figure 11B:
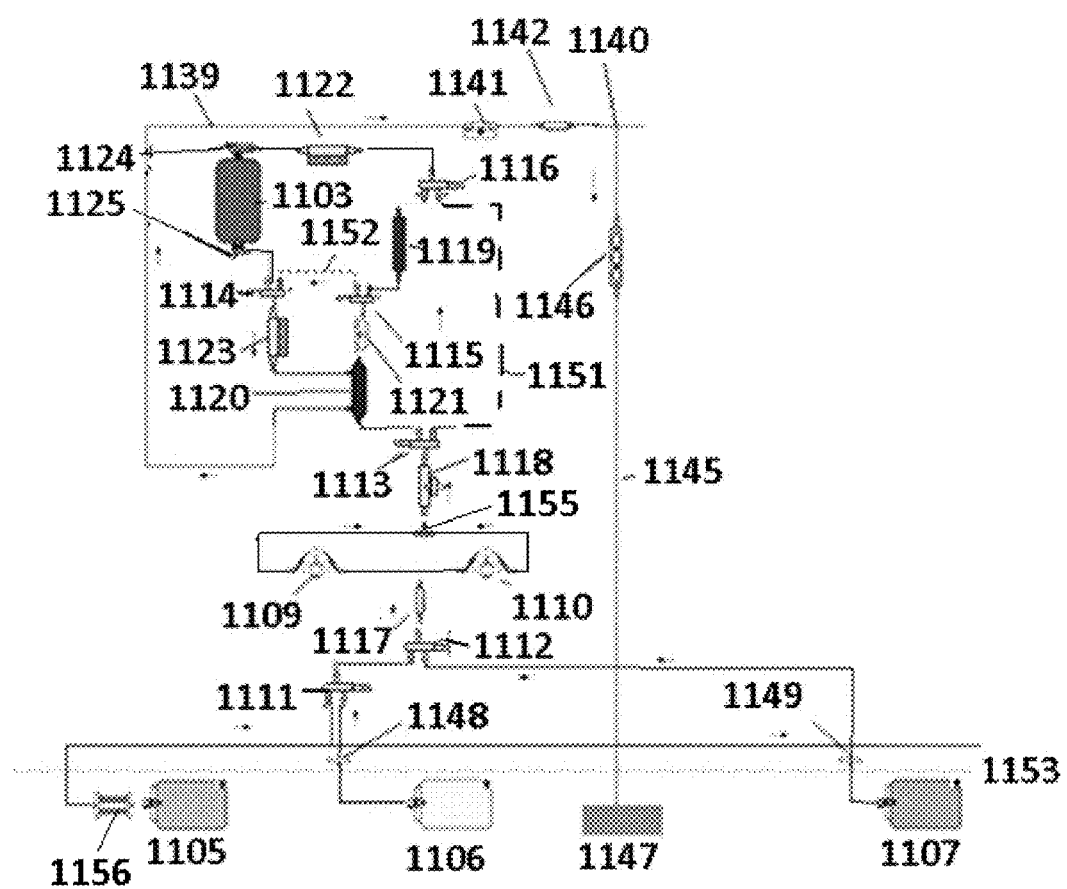
FIG. 11B shows a recharging flow path for recharging zirconium phosphate and is an exploded left side of FIG. 11A.
Figure 11C:
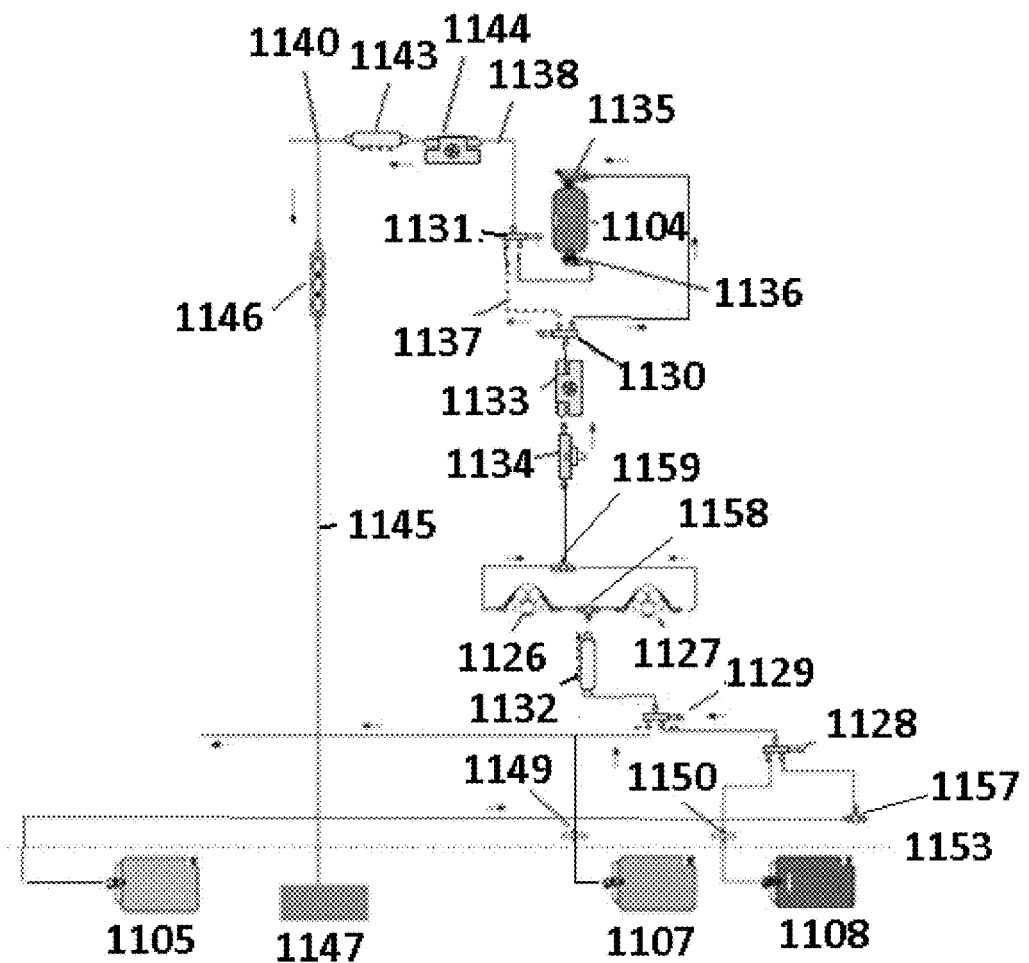
FIG. 11C shows a recharging flow path for recharging zirconium oxide and is an exploded right side of FIG. 11A.

To recharge the sorbent materials, fluids from fluid sources are passed through the sorbent modules. The flow paths of the invention can be arranged as shown in FIGS. 11A-C. FIG. 11A is a generalized view of a recharging flow path, with details shown in FIGS. 11B and 11C. The recharging flow path can be divided into a zirconium phosphate recharging flow path 1101 containing the zirconium phosphate module 1103 and a zirconium oxide recharging flow path 1102 containing zirconium oxide module 1104. Details of the zirconium phosphate recharging flow path 1101 on the zirconium phosphate side of line 1154 are illustrated in FIG. 11B, while details of the zirconium oxide recharging flow path 1102 on the zirconium oxide side of line 1154 are illustrated in FIG. 11C. Although a dual cartridge recharger system is shown, single, two or more multiple cartridge recharger systems are envisioned. Any one of the recharger cartridge systems can be linked together to share resources for recharging the sorbent cartridge and can be adapted for large scale use. Similarly, the linked rechargers can be scaled down as demand for recharging decreases. The modular recharging set-up having more or less rechargers based on demand can be advantageously used where required.

In FIG. 11A, a zirconium phosphate recharging flow path 1101 and a zirconium oxide recharging flow path 1102 have a water source 1105, a brine source 1106, a disinfectant source 1107, and a base source 1108. The brine source 1106, disinfectant source 1107, and/or base source 1108 can be a column containing a dry bed of the brine, disinfectant, and/or base components. Alternatively, a powdered source of the brine, disinfectant, and/or base components can be used. The dry bed or powdered source can be dissolved with an aqueous solution. A static mixer (not shown) can mix the single line coming through the column prior to entering the zirconium phosphate module 1103 or zirconium oxide module 1104. Recharging the zirconium phosphate in a zirconium phosphate module 1103 requires water, brine, and disinfectant. The water source 1105, the brine source 1106, and the disinfectant source 1107 are fluidly connected to the zirconium phosphate recharging flow path 1101. Similarly, recharging zirconium oxide module 1104 in zirconium oxide recharging flow path 1102 requires water, base, and disinfectant. The water source 1105, the disinfectant source 1107, and the base source 1108 are fluidly connected to the zirconium oxide recharging flow path 1102. The zirconium phosphate recharging flow path 1101 and zirconium oxide recharging flow path 1102 can be operated simultaneously or independently. Disinfectant source 1107 can contain any type of disinfectant compatible with zirconium phosphate and zirconium oxide that is capable of disinfecting the reusable sorbent modules. In any embodiment, the disinfectant source 1107 can contain peracetic acid. In any embodiment, the peracetic acid can be a solution of between 0.5% and 2% peracetic acid in water. The brine source 1106 can have an acid, a base, and a sodium salt.

During zirconium phosphate recharging, potassium, calcium, magnesium, and ammonium ions bound to the zirconium phosphate must be replaced by hydrogen and sodium ions. The final ratio of hydrogen to sodium ions on the recharged zirconium phosphate can be determined by the pH and sodium concentration of the brine solution used in the recharging process. The brine source 1106 can be a mixture of sodium chloride, sodium acetate, and acetic acid. In one non-limiting brine solution, the sodium chloride concentration can be between 2.5 M and 4.9 M, the sodium acetate concentration can be between 0.3 M and 1.1 M, and acetic acid concentration can be between 0.2 M and 0.8 M. The water source 1105 can contain any type of water, including deionized water. To recharge the zirconium phosphate in the zirconium phosphate module 1103, the disinfectant from disinfectant source 1107 can flow to the zirconium phosphate module 1103 to disinfect the zirconium phosphate module 1103. Fluid from the disinfectant source 1107 can flow to valve 1112 in the zirconium phosphate recharging flow path 1101. Zirconium phosphate pumps 1109 and 1110 provide a driving force to pump the fluid through the zirconium phosphate recharging flow path 1101. Use of two or more separate pumps can reduce wear on the pumps. Correspondingly, smaller pumps can be used. The two or more pumps can provide in-line mixing and intermittent pumping so at any given time, a single pump can pump fluid through the zirconium phosphate recharging flow path 1101. The two pumps can be used simultaneously or independently. The two or more pumps can provide fluid line mixing of one or more separate fluid streams when used simultaneously. The two or more pumps can operate asynchronously but used concurrently. For example, a first pump can operate for a time and a second pump remain off, then the first pump shut off with the second pump turning on. Multiple pumps at various timed pumping stages are envisioned as described herein. One of skill in the art will understand that a single zirconium phosphate pump can also accomplish the described pump functions.

Zirconium phosphate pumps 1109 and 1110 can pump fluid from disinfectant source 1107 through valve 1112 and valve 1113. Fluid can be pumped through three-way junction 1155 to valve 1116 and into zirconium phosphate module 1103 through zirconium phosphate module inlet 1124. The illustrated junctions combine the inlet chemical or water pumped by the two pumps such that higher flow rates can be achieved. During filling, fluid inside zirconium phosphate module 1103 can be forced through zirconium phosphate module outlet 1125 and into zirconium phosphate module effluent line 1139. The disinfectant can be sequestered in the zirconium phosphate module 1103 to ensure disinfection. Heater 1119 upstream of the zirconium phosphate module 1103 can heat the disinfectant because disinfection can become more efficient at elevated temperatures. After disinfection, zirconium phosphate module 1103 can be rinsed using water from water source 1105. Zirconium phosphate pumps 1109 and 1110 can pump water from water source 1105 through valves 1111 and 1112 to valve 1113. The water can then be pumped through valves 1115 and 1116 through the zirconium phosphate module 1103 through zirconium phosphate module inlet 1124, out zirconium phosphate module outlet 1125 and into zirconium phosphate module effluent line 1139. Water can be pumped through the zirconium phosphate module 1103 until all of the disinfectant is removed.

Fluid from brine source 1106 can be pumped through the zirconium phosphate module 1103 to load the zirconium phosphate module 1103 with the proper ratio of sodium and hydrogen ions. Zirconium phosphate pumps 1109 and 1110 can pump fluid from brine source 1106 to valve 1111. The brine can follow the same pathway as the water through zirconium phosphate module 1103 and into zirconium phosphate module effluent line 1139. Heater 1119 upstream of the zirconium phosphate module 1103 can heat brine because recharging can become more efficient at elevated temperatures. Heat exchanger 1120 can lessen the load on heater 1119. One or more heat exchangers and one or more heaters can be used. The heat exchanger 1120 can be fluidly connected to zirconium phosphate module effluent line 1139 and to zirconium phosphate module inlet 1124 upstream of heater 1119. The heated fluid exiting the zirconium phosphate module 1103 in zirconium phosphate module effluent line 1139 can heat the incoming brine solution in heat exchanger 1120. The heat exchanger 1120 can have at least a first chamber and a second chamber. Fluid in the zirconium phosphate inlet lines can pass through the first chamber of the heat exchanger 1120, and fluid in the zirconium phosphate effluent line 1139 can pass through the second chamber of the heat exchanger 1120. The increased temperature of the zirconium phosphate effluent in the second chamber can heat the fluid in the zirconium phosphate inlet lines in the first chamber. The zirconium phosphate module 1103 can be rinsed again by pumping water through the zirconium phosphate module 1103. A static mixer (not shown) can be positioned upstream of the zirconium phosphate module 1103 and mix the solutions prior to entering the zirconium phosphate module 1103.

Various sensors in the zirconium phosphate module recharging flow path 1101 can ensure proper concentrations and temperatures as shown in FIG. 11B. For example, conductivity sensor 1117 can ensure the incoming water contains no defined level of ions that may interfere with the recharging process, and that the brine solution and disinfectant solution are at a desired concentration. Conductivity sensor 1117 can also ensure sufficient rinsing has occurred to remove brine and disinfectant solution. Pressure sensor 1118 can monitor pressure in the zirconium phosphate inlet lines to ensure there are no occlusions or leaks and that the inlet pressures are in an acceptable range. Temperature sensor 1122 can ensure the brine solution is at the proper temperature before entering zirconium phosphate module 1103 and to control heater 1119. Temperature sensor 1123 can be placed in zirconium phosphate module effluent line 1139 to monitor the temperature of the effluent which can be controlled by heat exchanger 1120 and heater 1119. A flow sensor 1121 can monitor the flow rates of the fluids in the zirconium phosphate recharging flow path 1101 and control zirconium phosphate pumps 1109 and 1110. One of skill in the art will understand that alternative arrangements of sensors can be used in FIG. 11B and that one or more additional sensors can be added. Further, the sensors can be placed at any appropriate position in the zirconium phosphate recharging flow path 1101 to determine fluid parameters at various locations throughout the zirconium phosphate recharging flow path 1101.

Zirconium phosphate module bypass line 1152 fluidly connects valve 1115 to valve 1114 in the zirconium phosphate effluent line 1139. Valves 1115 and 1116 can be controlled to direct fluid through the zirconium phosphate module bypass line 1152 and into zirconium phosphate effluent line 1139. The dual flow path aspect of the recharging flow path depicted in FIG. 11A can neutralize the effluent from both the zirconium phosphate module 1103 and zirconium oxide module 1104 by mixing the acidic effluent from the zirconium phosphate module 1103 with the basic effluent from zirconium oxide module 1104. If only zirconium oxide module 1104 is being recharged using the flow path of FIG. 11C, the zirconium phosphate module bypass line 1152 can be utilized to direct fluid from the brine source 1106 to the zirconium phosphate effluent line 1139 to neutralize the zirconium oxide effluent without the need to simultaneously recharge a zirconium phosphate module 1103. Alternatively, zirconium phosphate module inlet 1124 can directly connect to zirconium phosphate module outlet 1125. The zirconium phosphate recharging flow path 1101 can include a rinse loop 1151 to fluidly connect valve 1113 upstream of the heater 1119 and heat exchanger 1120 to valve 1116, bypassing heater 1119 and heat exchanger 1120. The rinse loop 1151 can rinse brine solution from the zirconium phosphate module 1103. By bypassing heater 1119 and heat exchanger 1120 through rinse loop 1151, the zirconium phosphate module 1103 can be cooled faster.

To recharge the zirconium oxide module 1104, disinfectant from disinfectant source 1107 can be first pumped to the zirconium oxide module 1104 to disinfect the zirconium oxide module 1104. Fluid from the disinfectant source 1107 can be pumped to valve 1129 in the zirconium oxide recharging flow path 1102. Zirconium oxide pumps 1126 and 1127 can pump fluid through the zirconium oxide recharging flow path 1102. As described, a single zirconium oxide pump is contemplated as an alternative to the dual pump system in FIG. 11. Also, two or more zirconium oxide pumps are contemplated. The two or more zirconium oxide pumps can provide fluid line mixing of one or more separate fluid streams when used simultaneously. The two or more pumps can be asynchronous but used concurrently. For example, a first pump can operate for a time and a second pump remain off, then the first pump shut off with the second pump turning on. Multiple pumps at various timed pumping stages are envisioned as described herein. Zirconium oxide pumps 1126 and 1127 pump fluid from disinfectant source 1107 through valve 1129 to valve 1130. The fluid flows to the zirconium oxide module 1104 through zirconium oxide module inlet 1135. During filling, fluid inside zirconium oxide module 1104 can flow through zirconium oxide module outlet 1136 and into zirconium oxide module effluent line 1138. The disinfectant can be sequestered in zirconium oxide module 1104 to ensure disinfection. The zirconium oxide module 1104 can then be flushed with water from water source 1105 after disinfection is completed. Zirconium oxide pumps 1126 and 1127 can pump water from water source 1105 through valves 1128 and 1129 and junction 1157 to valve 1130. The fluid passes through junctions 1158 and 1159 to reach valve 1130. The water can then be pumped to zirconium oxide module 1104 through zirconium oxide module inlet 1135 and out zirconium oxide module outlet 1136 and into zirconium oxide module effluent line 1138. The zirconium oxide module 1104 can be flushed with any volume of water required to ensure the disinfectant is completely removed.

In FIG. 11C, zirconium oxide pumps 1126 and 1127 can pump fluid from base source 1108 through valve 1128 to zirconium oxide module 1104. The base source 1108 can contain hydroxide ions to recharge zirconium oxide module 1104. The hydroxide ions can flow through zirconium oxide module 1104 and into zirconium oxide module effluent line 1138. The base source 1108 can be any suitable basic solution capable of replacing phosphate and other anions bound to the zirconium oxide with hydroxide ions. The hydroxide base can be any suitable base such as sodium hydroxide. One non-limiting example is sodium hydroxide having a concentration between 0.5 M and 2.0 M. Another non-limiting example is sodium hydroxide having a concentration at greater than 2% of the concentration of the recharging solution, including any concentration between 2% and 50%, 2% and 5%, 5% and 10%, 5% and 20%, 10% and 25%, 15% and 35%, 20% and 50%, 30% and 40%, or 40% and 50%. A final rinse of the zirconium oxide module 1104 can be performed by pumping water through the zirconium oxide recharging flow path 1102 and zirconium oxide module 1104. Zirconium oxide recharging flow path 1102 can also have a zirconium oxide module bypass line 1137 fluidly connecting valve 1130 in the zirconium oxide inlet line to valve 1131 in the zirconium oxide effluent line 1138. Valves 1130 and 1131 can direct fluid through the zirconium oxide module bypass line 1137 and into zirconium oxide effluent line 1138. Zirconium oxide module bypass line 1137 can convey fluid directly from the base source 1108 to the zirconium oxide effluent line 1138 to neutralize the zirconium phosphate effluent without the need to simultaneously recharge a zirconium oxide module 1104. Alternatively, zirconium oxide module inlet 1135 can be fluidly connected to zirconium oxide module outlet 1136. Multiple sensors can be included in the zirconium oxide recharging flow path 1102 to monitor fluid concentration. For example, conductivity sensor 1132 can monitor concentrations of the zirconium oxide recharging fluid; pressure sensor 1134 can monitor pressure in the zirconium oxide inlet line and to detect leaks or occlusions. Flow sensor 1133 can determine the flow rate of the fluid through the zirconium oxide inlet line and control zirconium oxide pumps 1126 and 1127. A static mixer (not shown) can be positioned upstream of the zirconium oxide module 1104 and mix solutions prior to entering the zirconium oxide module 1104. A heater and heat exchanger (not shown) can be positioned in the zirconium oxide recharging flow path 1102 to heat fluids prior to entering zirconium oxide module 1104. Heating fluid in the zirconium oxide recharging flow path 1102 can reduce recharging times and allow disinfection with a base solution, such as sodium hydroxide. Heating the fluid also allows for reduced disinfection time with a disinfectant source. A zirconium oxide rinse loop (not shown) can also be included to bypass the heater and heat exchanger during flushing.

Effluent from zirconium phosphate recharging flow path 1101 can neutralize, either completely or in part, the effluent from zirconium oxide recharging flow path 1102, and vice versa. Zirconium phosphate effluent line 1139 can be fluidly connected to zirconium oxide effluent line 1138 at an effluent line junction 1140 joining drain line 1145, which fluidly connects to drain 1147. Static mixer 1146 at or downstream of the effluent line junction 1140 can mix zirconium phosphate effluent with zirconium oxide effluent.

Zirconium phosphate effluent line 1139 and zirconium oxide effluent line 1138 can be connected to a common reservoir for storage and disposal of the combined effluent. The common reservoir receives and collects the zirconium phosphate and zirconium oxide effluents together. The collected effluents can be drained after appropriate volumes of each effluent have been added to achieve neutralization. A common reservoir can allow for neutralization of the zirconium phosphate and zirconium oxide effluents without synchronizing the recharging processes. A single common reservoir can be sized to support multiple recharge stations.

Alternatively, the two fluid streams may be mixed through fluid line mixing at the effluent line junction 1140. Flow sensor 1141 and conductivity sensor 1142 can be placed in zirconium phosphate effluent line 1139 to measure the flow rate and composition of the zirconium phosphate effluent. Flow sensor 1144 and conductivity sensor 1143 can be positioned in the zirconium oxide effluent line 1138 to measure the flow rate and composition of the zirconium oxide effluent. Data from flow sensors 1141 and 1144 and conductivity sensors 1142 and 1143 can determine if the combined effluent in drain line 1145 is safe for disposal into a drain. One non-limiting example of safe is an effluent having a pH in the range of 5-9. Either zirconium phosphate effluent line 1139 or zirconium oxide effluent line 1138 can be connected simultaneously or independently to a waste reservoir (not shown) for disposal. Additional pH or conductivity sensors can be positioned downstream of the static mixer 1146 to monitor and ensure safe disposal. Drain line 1145 can also be connected to a common waste reservoir for storage and disposal of effluent. The common reservoir receives and collects the zirconium phosphate and zirconium oxide effluents together. The collected effluents can be drained after appropriate volumes of each effluent have been added to achieve neutralization. A common waste reservoir advantageously allows for neutralization of the zirconium phosphate and zirconium oxide effluents without synchronizing the recharging processes. Static mixer 1146 is unnecessary when a common reservoir is used.

Brine source 1106, disinfectant source 1107, and base source 1108 can have filter 1148, filter 1149, and filter 1150, respectively to remove particulate matter. The one or more filters can remove particulate matter before fluid enters the zirconium oxide recharging flow path 1102 or zirconium phosphate recharging flow path 1101. Water source 1105 can have microbial filter 1156 to remove microbes from the water before entering the flow paths. In FIG. 11C, the dashed line 1153 represents a recharger housing. The fluid sources can be external to the recharger housing and fluidly connected to the lines located inside of the recharger housing. Alternatively, the fluid sources described can instead be housed within the recharger.

During recharging, fluid can be passed through the zirconium phosphate module 1103 and/or the zirconium oxide module 1104 opposite to a flow direction used during dialysis. For example, zirconium phosphate module inlet 1124 can be the zirconium phosphate module outlet during dialysis, and zirconium phosphate module outlet 1125 can be the zirconium phosphate module inlet during dialysis in FIG. 11B. Similarly, zirconium oxide module inlet 1135 can be the zirconium phosphate module outlet during dialysis, and zirconium oxide module outlet 1136 can be the zirconium phosphate module inlet during dialysis. Pumping the recharging fluid through the modules in the opposite direction relative to dialysis can improve the efficiency of the recharging process.

The zirconium phosphate recharging flow path 1101 or zirconium oxide recharging flow path 1102 can independently recharge zirconium phosphate or zirconium oxide. For example, a single flow path fluidly connecting zirconium phosphate module 1103 of FIG. 11B via valve 1112 and valve 1113 to each of the water source 1105, brine source 1106, and disinfectant source 1107 can independently recharge the zirconium phosphate module 1103. Similarly, a single flow path fluidly connecting zirconium oxide module 1104 of FIG. 11C via valve 1128 and valve 1129 to each of the water source 1105, disinfectant source 1107, and base source 1108 can independently recharge the zirconium oxide module 1104.

The water source 1105, brine source 1106, disinfectant source 1107, and base source 1108 can recharge one or more reusable sorbent module of various sizes. The amount of water, brine, disinfectant, and base depends on the concentration of each of the recharging solutions, the size of the reusable sorbent modules, the amount of cations/anions removed, and the flow rate used to pass the solutions through the reusable modules. The amount of brine solution required can depend on the temperature to which the brine solution is heated. For example, a brine solution having between 2.5 M and 4.9 M sodium chloride, between 0.3 M and 1.1 M sodium acetate, and between 0.2 M and 0.8 M acetic acid at between 65° C. and 95° C. requires between 4.2-6.2 L of brine to recharge a zirconium phosphate module containing between 2 kg and 3.2 kg of zirconium phosphate loaded with 2 to 3 moles of ammonium, calcium, magnesium and potassium. The brine solution should have a volume of at least between 4.2 and 6.2 L and delivered at a flow rate of between 100 and 300 mL/min. A single brine source can be connected to multiple rechargers, or can recharge multiple zirconium phosphate modules in a single recharger. The brine source can have a significantly larger volume from 1-100× or greater to ensure the brine source need not be refilled each time a zirconium phosphate is recharged. For a zirconium oxide module having between 220 and 340 g of zirconium oxide loaded with 200 mmols of phosphate, a base source having between 0.5 and 2.0 M sodium hydroxide and a flow rate between 30 and 150 mL/min requires between 1 and 4 L of base. The base source can be at least between 1 and 4 L in volume. For recharging multiple zirconium oxide modules, a larger base source can be used.

Figure 12A:
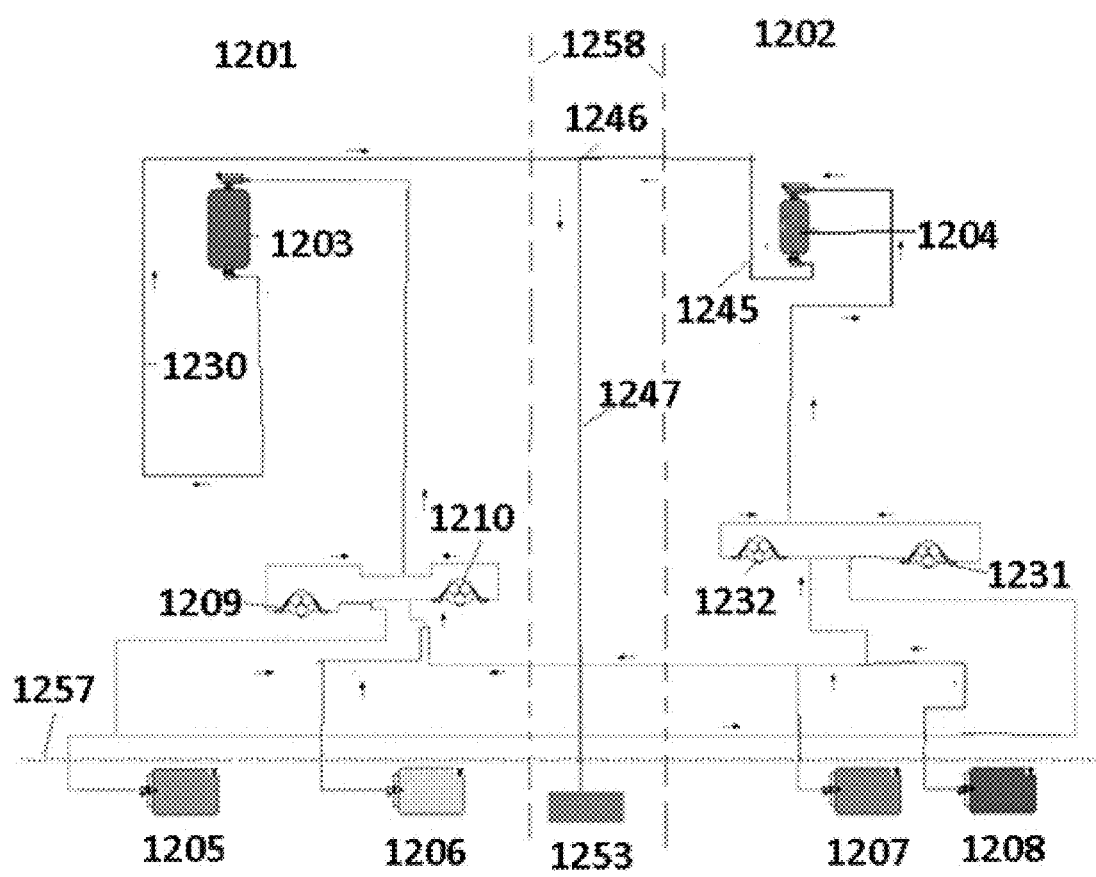
FIG. 12A shows a recharging flow path for recharging zirconium phosphate and zirconium oxide with inline mixing of recharging solutions.
Figure 12B:
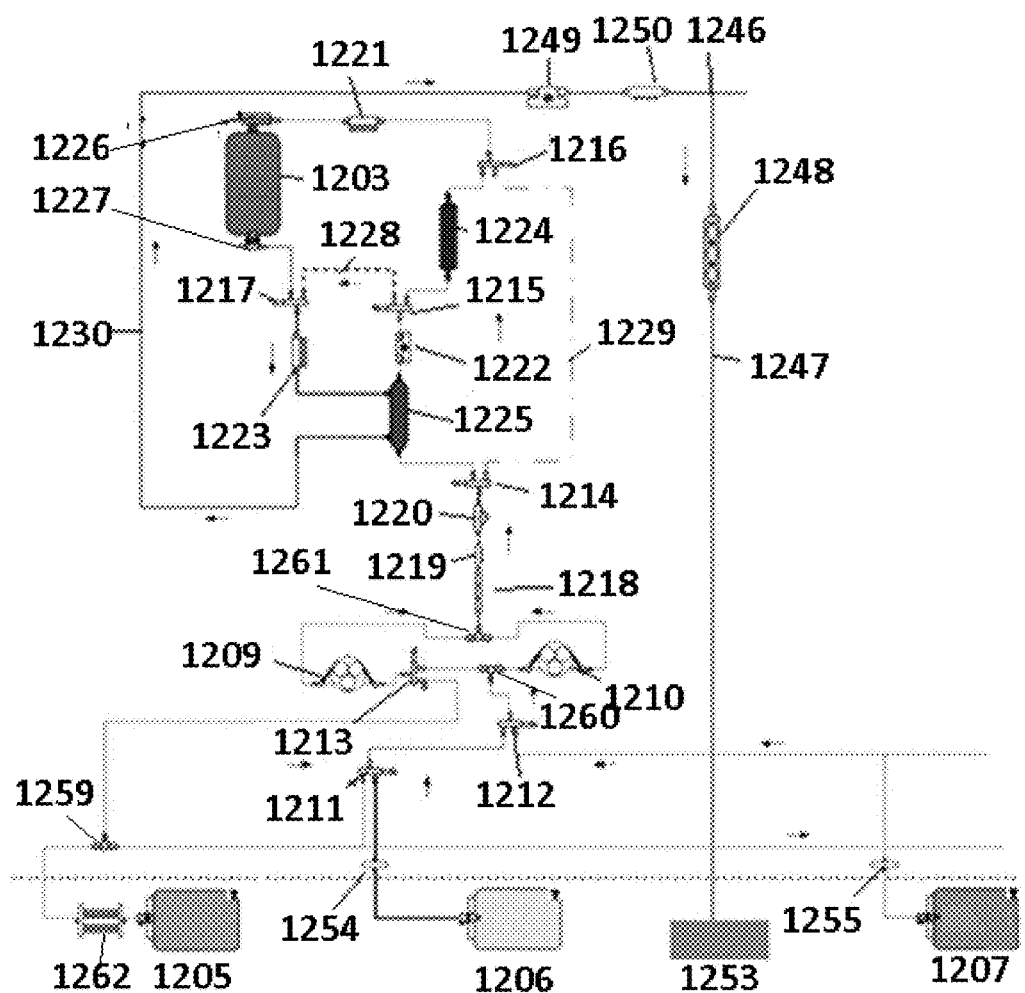
FIG. 12B shows a recharging flow path for recharging zirconium phosphate with inline mixing of recharging solutions and is an exploded right side of FIG. 12A.
Figure 12C:
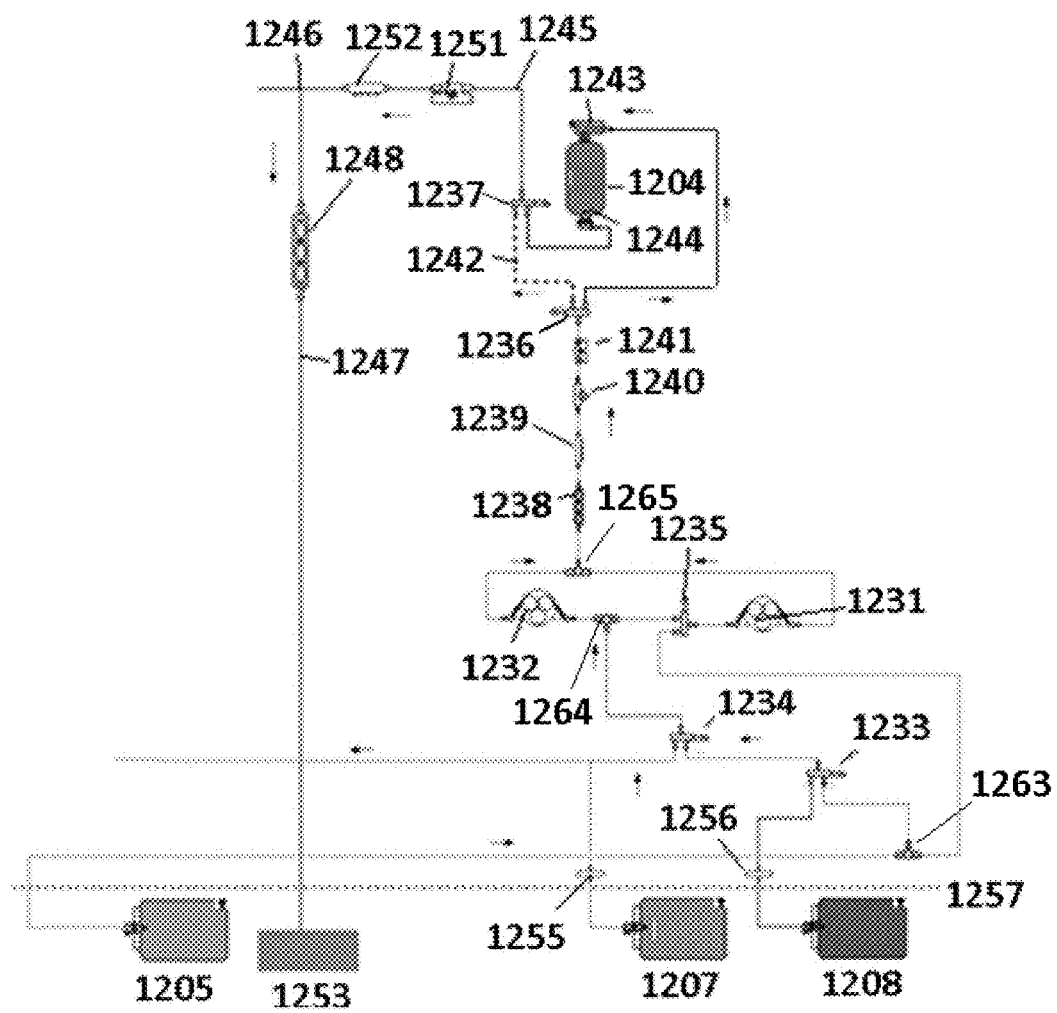
FIG. 12C shows a recharging flow path for recharging zirconium oxide with inline mixing of recharging solutions and is an exploded left side of FIG. 12A.

FIG. 12A is a generalized view of a recharging flow path having a zirconium phosphate recharging flow path 1201 containing a zirconium phosphate module 1203 and a zirconium oxide recharging flow path 1202 containing a zirconium oxide module 1204. FIG. 12B illustrates a detailed view of zirconium phosphate recharging flow path 1201 on the zirconium phosphate side of line 1258, and FIG. 12C illustrates a detailed view of zirconium oxide recharging flow path 1202 on the zirconium oxide side of line 1258. The valves, pumps and static mixers illustrated in FIGS. 12B and 12C allow for inline mixing of the recharging fluids. In FIG. 12A, the zirconium phosphate recharging flow path 1201 and/or zirconium oxide recharging flow path 1202 can be simultaneously or independently connected to a water source 1205, a brine source 1206, a disinfectant source 1207, and a base source 1208. Because recharging of the zirconium phosphate in a zirconium phosphate module 1203 can require water, brine, and disinfectant, and because recharging of zirconium oxide in zirconium oxide module 1204 can also require water, base, and disinfectant, the water source, 1205, the brine source 1206, and the disinfectant source 1207 can be jointly connected to the zirconium phosphate recharging flow path 1201, and the water source 1205, the disinfectant source 1207, and the base source 1208 can be jointly connected to the zirconium oxide recharging flow path 1202.

In FIG. 12A, zirconium phosphate recharging flow path 1201 and zirconium oxide recharging flow path 1202 can mix chemicals in-line to create the recharging solutions. Any one of disinfectant source 1207, brine source 1206, and base source 1208 can contain solutions having concentrations over the concentration of the components to be used in recharging the reusable modules. Water source 1205 can dilute the disinfectant, brine, and base from the fluid sources prior to recharging. In FIG. 12B, zirconium phosphate pump 1210 can pump disinfectant into the zirconium phosphate module 1203 with in-line mixing of concentrated disinfectant from disinfectant source 1207 from valve 1212 through junctions 1260 and 1261 and into static mixer 1218. Concurrently, zirconium phosphate pump 1209 can pump water through junction 1259 and valve 1213 and into static mixer 1218 from water source 1205. Alternatively, the concentrated disinfectant and water can be mixed through fluid line mixing at the junction of the two fluid lines. The zirconium phosphate pumps 1209 and 1210 can pump a disinfectant solution having a specified concentration and composition to disinfect the zirconium phosphate module 1203 via valves 1212 and 1213. The disinfectant solution can flow from static mixer 1218 through valve 1214 to valve 1216 and then into the zirconium phosphate module 1203 through zirconium phosphate module inlet 1226. Fluid can exit zirconium phosphate module 1203 through zirconium phosphate module outlet 1227 into zirconium phosphate effluent line 1230. After disinfection of zirconium oxide module 1203, zirconium phosphate pumps 1209 1210 can pump water from water source 1205 into zirconium phosphate module 1203. For example, zirconium phosphate pump 1209 can pump water through valve 1213 to zirconium phosphate module 1203 while zirconium phosphate pump 1210 can pump water through valves 1211 and 1212 to zirconium phosphate module 1203. Alternatively, zirconium phosphate pump 1209 can pump water through valves 1211, 1212, and 1213 while zirconium phosphate pump 1210 pumps water through valves 1211 and 1212. During recharging, zirconium phosphate pumps 1209 and 1210 can pump brine through valve 1211 to valve 1212 from brine source 1206 into static mixer 1218. If a concentrated brine solution is being used, zirconium phosphate pumps 1209 and/or 1210 can pump water from water source 1205 to static mixer 1218 to dilute the brine solution and generate a brine solution having a proper solute concentration for recharging the zirconium phosphate. After pumping brine through the zirconium phosphate module 1203, zirconium phosphate pump 1209 can pump water through valves 1211, 1212 and 1213 while zirconium phosphate pump 1210 can pump water through valve 1211 and 1212.

The zirconium phosphate recharging flow path 1201 of FIG. 12B can have a heater 1224 and heat exchanger 1225. One or more heat exchangers and one or more heaters can be used. The brine solution can be heated by the heater 1224 upstream of the zirconium phosphate module 1203. Heat exchanger 1225 can utilize the heat from brine exiting the zirconium phosphate module 1203, to heat the incoming brine solution upstream of heater 1224 to reduce the burden on heater 1224. As described, the zirconium phosphate recharging flow path 1201 can also have an optional zirconium phosphate module bypass line 1228 fluidly connecting valve 1215 in the zirconium phosphate inlet line to valve 1217 in the zirconium phosphate effluent line 1230. The zirconium phosphate module bypass line 1228 can neutralize the zirconium oxide effluent with brine even if the zirconium phosphate module 1203 is not being recharged. Zirconium phosphate recharging flow path 1201 can have a rinse loop 1229 connecting valve 1214 upstream of the heater 1224 and heat exchanger 1225 to valve 1216 to bypass heater 1224 and heat exchanger 1225 to rinse brine out of the zirconium phosphate module 1203.

Various sensors can be included in the zirconium phosphate recharging flow path 1201 to ensure fluid parameters are within acceptable ranges. In FIG. 12B, conductivity sensor 1219 can be placed downstream of static mixer 1218 to ensure mixing and specified recharging fluid concentrations. Pressure sensor 1220 can measure the fluid pressure and to identify leaks or occlusions. Flow sensor 1222 can determine the flow rate of the fluid entering the zirconium phosphate module 1203 and control zirconium phosphate pumps 1209 and 1210. Temperature sensor 1221 can determine if the recharging fluid is a proper temperature range upon entering zirconium phosphate module 1203 and relay data to a processor (not shown) that can control heater 1224. Temperature sensor 1223 can determine the temperature of the zirconium phosphate effluent prior to entering heat exchanger 1225. Other sensor arrangements, including any number of conductivity, pressure, flow, and temperature sensors can be used.

In FIG. 12C, zirconium oxide pump 1232 can pump disinfectant from disinfectant source 1207 through valve 1234 and into static mixer 1238 to disinfect the zirconium oxide module 1204 in zirconium oxide recharging flow path 1202. Zirconium oxide pump 1231 can pump water from water source 1205 through valve 1235 to static mixer 1238 to dilute the disinfectant from disinfectant source 1207 to provide in-line mixing of the disinfectant solution. The diluted disinfectant can then be pumped through valve 1236 to zirconium oxide module inlet 1243 and into zirconium oxide module 1204. Effluent from the zirconium oxide module 1204 can exit through zirconium oxide module outlet 1244 and into zirconium oxide effluent line 1245. After disinfection, the disinfectant can be rinsed from the zirconium oxide module 1204 by pumping water from water source 1205 through valve 1235 to zirconium oxide module 1204 by zirconium oxide pump 1231 while zirconium oxide pump 1232 pumps water through valves 1233 and 1234 to zirconium oxide module 1204. Alternatively, zirconium oxide pump 1231 can pump water through valves 1233, 1234, and 1231, while zirconium oxide pump 1232 pumps water through valves 1233 and 1234. To recharge zirconium oxide module 1204, zirconium oxide pump 1232 can pump base from base source 1208 through valves 1233 and 1234 through junctions 1264 and 1265 to static mixer 1238. Water from water source 1205 can be pumped by zirconium oxide pump 1231 through junctions 1263 and 1265 into static mixer 1238 to dilute the base by in-line mixing. Alternatively, the water and base can be mixed through fluid line mixing at the junction of the two fluid lines. Alternatively, the base can be pre-set using specified amounts of base in pre-packaged packets or containers. Diluted base can flow through the zirconium oxide recharging flow path 1202 and through zirconium oxide module 1204. The zirconium oxide module 1204 can be rinsed any numbers of times, as needed, by introducing water from water source 1205 to the zirconium oxide module 1204. The zirconium oxide recharging flow path 1202 can also have a zirconium oxide module bypass line 1242 that fluidly connects valve 1236 to valve 1237 in the zirconium oxide effluent line 1245 to bypass zirconium oxide module 1204. In this way, zirconium phosphate effluent can be neutralized with a base solution even if the zirconium oxide module 1204 is not being recharged. A heater and heat exchanger (not shown) can be positioned in the zirconium oxide recharging flow path 1202 to heat fluids prior to entering zirconium oxide module 1204. A zirconium oxide rinse loop (not shown) can also be included to bypass the heater and heat exchanger. Similarly, the zirconium oxide recharging flow path 1202 can also have sensors for measurement and control over the recharging process. In FIG. 12C, a conductivity sensor 1239 can be placed downstream of static mixer 1238 to ensure that diluted recharging solutions have a desired concentration. Pressure sensor 1240 can detect the pressure in the zirconium oxide recharging flow path 1202 to detect leaks or occlusions. Flow sensor 1241 can detect the flow rate of fluid in the zirconium oxide recharging flow path 1202 and can to control zirconium oxide pumps 1231 and 1232.

As shown in FIG. 12A, the present invention can provide in-line neutralization of the effluent from each of the zirconium phosphate recharging flow path 1201 and zirconium oxide recharging flow path 1202. The zirconium phosphate effluent line 1230 can be fluidly connected to zirconium oxide effluent line 1245 at effluent line junction 1246 and fluidly connected to drain line 1247. As shown in FIGS. 12B and 12C, a static mixer 1248 can be positioned at or downstream of the effluent line junction 1246 to ensure mixing of the effluents from the zirconium phosphate recharging flow path 1201 and zirconium oxide recharging flow path 1202. The combined effluent can be passed through the drain line 1247 to drain 1253, a common waste reservoir (not shown), or separate waste reservoirs. A conductivity sensor 1250 as shown in FIG. 12B in zirconium phosphate effluent line 1230 and a conductivity sensor 1252 as shown in FIG. 12C in zirconium oxide effluent line 1245 can determine the composition of the effluents. Flow sensor 1249 in zirconium phosphate effluent line 1230 of FIG. 12B and flow sensor 1251 in zirconium oxide effluent line 1245 of FIG. 12C can be used simultaneously or independently to measure the flow rates of each of the effluents. Determining the composition of the effluent fluids as well as the respective flow rates using one or more sensors described can monitor the system function and ensure he combined effluent in drain line 1247 is safe for disposal or storage.

Brine source 1206, disinfectant source 1207, and base source 1208 can have filter 1254, filter 1255, and filter 1256, respectively to remove particulate matter prior to entering zirconium phosphate recharging flow path 1201 or zirconium oxide recharging flow path 1202. The filters can also act as inline mixers to mix the solutions. Water source 1205 can have microbial filter 1262 to remove microbes from the water source 1205. Brine source 1206, disinfectant source 1207, and base source 1208 can be housed outside of a recharger housing denoted by line 1257. The brine solution, disinfectant solution, and base solution can be generated through in-line mixing as described. Alternatively, pre-mixed solutions, concentrates, or infusates can be introduced into brine source 1206, disinfectant source 1207, and base source 1208 and delivered to zirconium phosphate recharging flow path 1201 or zirconium oxide recharging flow path 1202. For example, the brine solution in brine source 1206 can be pre-mixed or provide in pre-packaged amounts in the proper concentrations and introduced into brine source 1206, disinfectant source 1207, and base source 1208.

In-line mixing can provide higher concentrations of solutes, lower fluid volumes required by the system, and physically smaller fluid reservoirs. The fluids should have suitable concentrations for use in the zirconium phosphate recharging flow path 1201 or zirconium oxide recharging flow path 1202. For example, an initially high source of disinfectant, such as peracetic acid, can be used in a concentration of between 20% and 40%. The zirconium phosphate recharging flow path 1201 of FIG. 12B can dilute the peracetic acid source by a factor of 20:1 to 40:1 to generate a disinfectant recharging solution having a concentration between 0.5% and 2%. In one embodiment the initial disinfectant concentration can be 32%. The initial disinfectant concentration can be any concentration greater than 1%. Similarly, the base solution can be sodium hydroxide having an initial concentration between 14 M and 22 M. The zirconium oxide recharging flow path 1202 of FIG. 12C can dilute the base solution by 18:1 to 22:1 to generate a base solution having a concentration between 0.8 and 1.0 M. In one embodiment the initial base concentration can be 6 M. The initial base solution concentration can be any concentration greater than or equal to 0.5 M. The brine solution can also be diluted in-line to generate a brine solution having a proper recharging concentration. The brine source 1206 of FIG. 12A can be one or more reservoirs. For example, an acetic acid source, a sodium acetate source and a sodium chloride source can each be connected in place of single brine source 1206. Alternatively, an acetic acid source, a base source, and a sodium chloride source can be connected in place of the single brine source 1206 with mixing of the base and acetic acid to generate the sodium acetate. The individual components can be added to the zirconium phosphate recharging flow path 1201 in the proper ratios to generate the recharging brine.

The chemicals used in the recharging process can be packaged and shipped in any form. The chemicals can be packaged and shipped as solutions, either in proper concentrations for use in recharging or with higher concentrations for use in inline mixing. In any embodiment, the chemicals may be packaged and shipped in pure form, such as 100% acetic acid or solid sodium chloride, sodium acetate, or sodium hydroxide.

Figure 13:
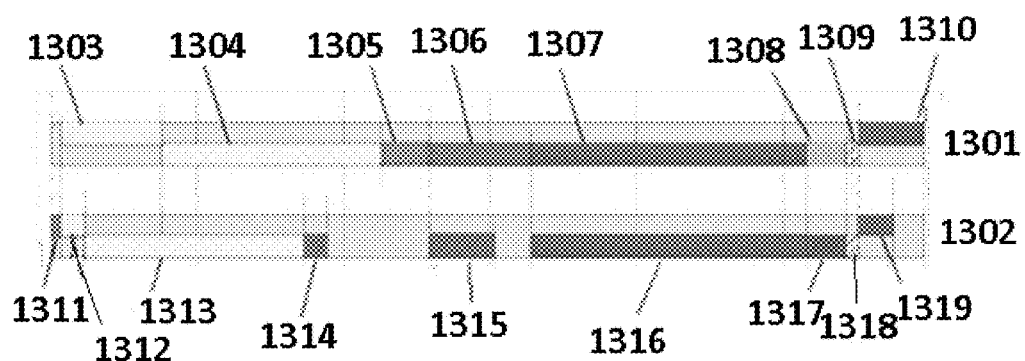
FIG. 13 shows a timeline for concurrent recharging of zirconium oxide and zirconium phosphate.

FIG. 13 illustrates a non-limiting example of a timeline that can be used for concurrent or separate recharging of zirconium phosphate and zirconium oxide. The steps illustrated in FIG. 13 are generalized times for the specific actions illustrated in FIGS. 1-10. Timeline 1301 shows recharging zirconium phosphate and timeline 1302 shows recharging zirconium oxide. As illustrated in timeline 1301, the zirconium phosphate recharging process can begin by introducing a disinfectant, such as peracetic acid, into the zirconium phosphate module, shown as step 1303. The time necessary to fill the zirconium phosphate module with the disinfectant can depend on the flow rate of the disinfectant solution and the volume of the zirconium phosphate module. The disinfectant can be delivered to the zirconium phosphate module in step 1303 at a flow rate of between 100 and 500 mL/min, which can fill a zirconium phosphate module in a time of between 5-10 minutes. Longer or shorter flushing times can be used depending on the need. After filling the zirconium phosphate with the disinfectant solution, the disinfectant solution can be held in the zirconium phosphate module to ensure disinfecting of the zirconium phosphate module in step 1304. In any embodiment, the disinfectant can be held in the zirconium phosphate module for any length of time sufficient to disinfect the zirconium phosphate module, including between 5 and 20 minutes. The temperature of the disinfectant can be determined with a temperature sensor, and the hold time adjusted as necessary. For example, if the disinfectant temperature is 22° C., the hold time can be 5 minutes. The disinfectant can also be heated to minimize the necessary hold time by heating the disinfectant to room temperature if necessary. During the hold time, the disinfectant flow can be stopped or reduced to a low flow condition, such as 5 to 75 ml/min. Holding the disinfectant in the module can build up pressure in the module, requiring periodic venting. To maintain the volume after venting, during which some fluid may leak, the disinfectant can be pumped into the module at a low flow rate during the venting. Alternatively, during the hold time, the disinfectant flow rate can be set to between 5 and 75 ml/min to prevent pressure buildup while maintaining fluid volume in the modules. The disinfectant solution can then be flushed from the zirconium phosphate module in step 1305 by pumping water through the zirconium phosphate module. The water can flow through the zirconium phosphate module at a specified rate. A higher flow rate of the water in step 1305 will cause a quicker flush time. The water can be pumped through the zirconium phosphate module at a rate of between 300 and 500 mL/min. Depending on the size of the zirconium phosphate module, the zirconium phosphate module can be flushed in about 5-10 minutes. As described, the system can utilize one or more sensors, such as pH sensors or conductivity sensors in the zirconium phosphate effluent lines to determine if disinfectant is fully flushed in step 1305. After flushing the disinfectant from the zirconium phosphate module in step 1305, brine solution can be pumped through the zirconium phosphate module to recharge the zirconium phosphate module starting in step 1306. The brine solution can be pumped through the zirconium phosphate module in step 1306 at any rate. One of skill in the art will understand that a higher flow rate of brine solution may decrease the time necessary to recharge the zirconium phosphate, but may also decrease the efficiency of the process, resulting in the need for additional brine. Conductivity or pH sensors can determine if the zirconium phosphate module has been fully filled with brine.

The brine flow rate can be set to any flow rate, including between 150 and 250 mL/min. Depending on the size of the zirconium phosphate module, between 5 and 10 minutes may be needed for brine to reach the sensors in the zirconium phosphate effluent line. Once brine has reached the sensors in the effluent line, the brine can flow through the zirconium phosphate module in step 1307 until recharging is complete. Recharging time can vary based on the flow rate of the brine solution, the concentration of the brine solution, and the temperature of the brine solution. For example, the brine solution can be heated during the recharging process between 65° C. and 95° C. Recharging of zirconium phosphate can be more efficient at elevated temperatures. Conductivity sensors can determine if step 1308 has been completed by detecting the conducting of the fluid in the zirconium phosphate effluent line. If the conductivity of the effluent matches the conductivity of the brine, then no additional ions from the brine are being exchanged onto the zirconium phosphate, and recharging is complete. For example, steps 1308, 1309, and 1310 represent brine solution being flushed from the zirconium phosphate module with water. Flushing can continue through step 1310 until the conductivity sensors in the zirconium phosphate effluent line determine no additional brine is being removed from the zirconium phosphate module.

As depicted in timeline 1302, zirconium oxide can be recharged concurrently or independently of zirconium phosphate. In step 1311, zirconium oxide recharging begins by rinsing the zirconium oxide module with water. The water rinse can flush leftover dialysate bicarbonate or any sodium hydroxide from the flow loop, which react violently with acid necessary for disinfection. After flushing the zirconium oxide module with water in step 1311, disinfectant solution can be delivered to disinfect the module in step 1312. The time necessary to fill the zirconium oxide module with disinfectant depends on the size of the zirconium oxide module and the flow rate of the disinfectant. Because less zirconium oxide is needed for dialysis than zirconium phosphate, the zirconium oxide module may be smaller than the zirconium phosphate module, and therefore fill faster in step 1312 as compared to the zirconium phosphate module in step 1303. Upon filling, the disinfectant can be sequestered in the zirconium oxide module to allow for disinfection in step 1313. The disinfectant can be held in the zirconium oxide module for any length of time, including between 5 and 20 minutes. The temperature of the disinfectant can be determined with a temperature sensor, and a hold time adjusted as necessary. For example, if the disinfectant temperature is 22° C., the hold time can be 5 minutes. The disinfectant can also be heated to minimize the necessary hold time. Upon disinfection, the disinfectant can be flushed from the zirconium oxide module in step 1314.

In step 1315 the base solution flows through the zirconium oxide module to recharge the zirconium oxide. Step 1315 continues until a basic solution is detected in the zirconium oxide effluent line. During simultaneous recharging, the basic effluent from the zirconium oxide recharging flow path neutralizes the acidic effluent from the zirconium phosphate recharging flow path. Once a basic effluent is detected in step 1315, the zirconium oxide recharging process can be halted until the acid brine is detected in the effluent of the zirconium phosphate module in step 1306, which may occur later due to size differences of the zirconium phosphate and zirconium oxide modules. After the acidic effluent is detected in the zirconium phosphate module, shown as step 1306, the base can continue to flow through the zirconium oxide module in step 1316. The flow rate of the base solution in step 1316 can be any suitable rate. For example, the flow rate of the base solution can be between 30 and 150 mL/min. To ensure neutralization, the flow rate of the base in step 1316 can depend on the flow rate of the brine in step 1307. A neutralization ratio can be calculated based on the relative pH, buffer capacity and concentration of the zirconium phosphate effluent and zirconium oxide effluent. For example, a neutralization ratio of 1.5:1 means that 1.5 liters of the zirconium phosphate effluent will be required to fully neutralize one liter of zirconium oxide effluent. The flow rate of the base in step 1316 can be set to half the flow rate of the brine solution, allowing full neutralization of both solutions. For example, the flow rate of the base in step 1316 can be between 75 and 125 mL/min if the neutralization ratio is 1.5:1 and the brine flow rate is between 150 and 250 mL/min.

After the brine solution is detected in the effluent of the zirconium phosphate and the flushing of the brine begins in step 1308, the base solution can pass through the zirconium oxide module, shown as step 1317 until the brine is mostly or fully flushed from the zirconium phosphate module, shown as step 1309. At this point, the base solution can be flushed from the zirconium oxide module, shown as step 1318. After confirming that the base has been flushed from the zirconium oxide module, flushing is completed in step 1319.

One of skill in the art will understand that the times and flow rates described in FIG. 13 can be altered within the scope of the invention. Higher flow rates can cause faster recharging of the modules. Times can be decreased by using more concentrated solutions, but may decrease efficiency. Specified concentrations, flow rates, and times can be set per the needs of the user, taking into account the cost of chemicals and need for fast recharging. The times and flow rates shown in zirconium oxide recharging timeline 1302 can also be altered to reduce idle time. For example, the flow rate of the base solution in step 1315 can be slowed down to reduce the time gap between steps 1315 and 1316. If a single sorbent module is being recharged independently, or if a common waste reservoir either inside or outside of the recharger is used for the zirconium phosphate and zirconium oxide recharging flow paths, the times and flow rates shown in FIG. 13 can be adjusted. Synchronizing the zirconium phosphate timeline 1301 with the zirconium oxide timeline 1302 is unnecessary because effluent is no longer neutralized in-line.

The zirconium oxide and zirconium phosphate sorbent modules can be recharged and reused any number of times. Alternatively, the sorbent modules may have a defined useful life, including a maximum number of recharge and reuse cycles. When a sorbent module reaches the end of the sorbent module's useful life, the sorbent module can be recycled or disposed of. A disinfection only cycle can disinfect the sorbent modules for safe disposal and/or recycling at the end of the sorbent module's useful life. In a disinfection only cycle, the disinfectant can be pumped into the sorbent module as described but the other recharge solutions would not be used. After disinfection, and optionally rinsing of the sorbent module, the sorbent module can be disposed or recycled safely.

Figure 14:
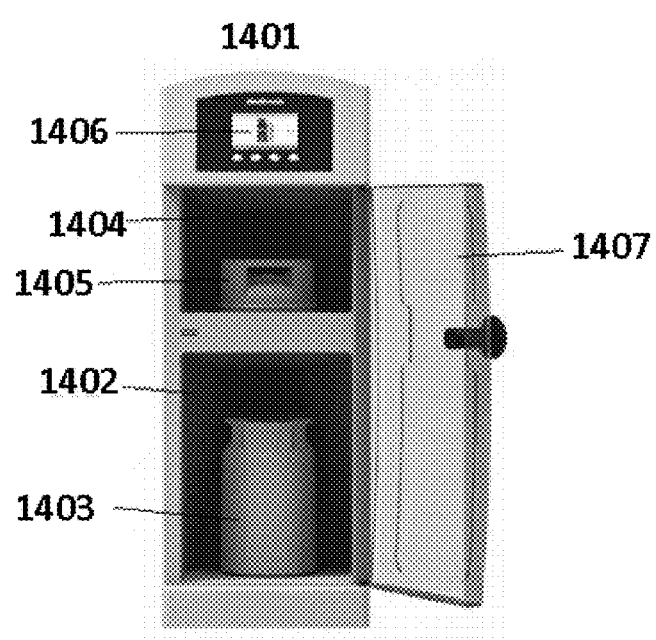
FIG. 14 shows a recharger for recharging zirconium phosphate and zirconium oxide modules.

The rechargers described can be configured as shown in FIG. 14. The recharger 1401 includes a receiving compartment 1402 for receiving a reusable zirconium phosphate module 1403. Fluid connections (not shown in FIG. 14) connect to the top and bottom of the zirconium phosphate module 1403 for passing recharging fluids into, through, and out of the reusable sorbent module 1403. The recharging fluids replace ions bound to the sorbent materials during dialysis with new ions, recharging the zirconium phosphate within the zirconium phosphate module 1403, allowing reuse of the zirconium phosphate module 1403 in dialysis. The recharger 1401 also has a second receiving compartment 1404 for receiving a reusable zirconium oxide module 1405, which is also fluidly connected to recharging fluid sources for recharging of the zirconium oxide module 1405. The recharger 1401 can be configured to concurrently recharge a zirconium phosphate module 1403 and a zirconium oxide module 1405, or to independently recharge either a zirconium phosphate module 1403 or a zirconium oxide module 1405. A user interface 1406 is provided to start or control the recharging process by the user. The user interface 1406 also provides the status of the recharging process to the user, such as the times of completion of each recharging step, or a time until the recharging process is complete. User interface 1406 also provides alert messages if any problems are detected during recharging, such as leaks, occlusions, pump failures, or mismatched chemicals. A door 1407 on the recharger 1401 controls access to the receiving compartments 1402 and 1404 during operation.

As shown in FIG. 14, the receiving compartments 1402 and 1404 may be of different sizes. Because less zirconium oxide is needed for dialysis than zirconium phosphate, the zirconium oxide module 1405 is smaller than the zirconium phosphate module 1403 and the receiving compartments 1402 and 1404 are sized accordingly. The zirconium phosphate receiving compartment 1402 is larger than the zirconium phosphate module 1403 and the zirconium oxide receiving compartment 1404 is larger than the zirconium oxide module 1405. The larger space allows a user room to maneuver the fluid connectors and sorbent modules to connect the inlets and outlets on the sorbent modules to the inlets and outlets on the recharger. Rechargers with any number of receiving compartments for recharging any number or combination of zirconium oxide and/or zirconium phosphate sorbent modules can be constructed. For example, a recharger with two zirconium phosphate receiving compartments and two zirconium oxide receiving compartments can be similarly constructed. The rechargers can have 1, 2, 3, 4, 5, 6, or more receiving compartments, each capable of receiving zirconium oxide or zirconium phosphate sorbent modules.

Figure 15:
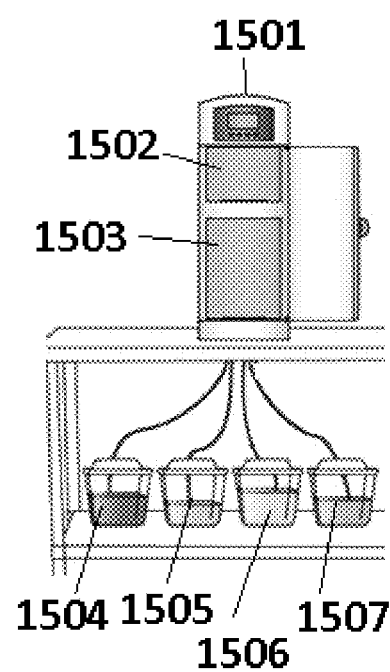
FIG. 15 shows a recharger fluidly connected to external fluid sources.

FIG. 15 illustrates non-limiting embodiment of a recharger set up for recharging zirconium oxide and zirconium phosphate, either concurrently or independently. To recharge the sorbent materials, one or more recharging fluids are passed through the reusable sorbent modules. As shown in FIG. 15, the recharger 1501 is fluidly connected to one or more recharging fluid sources, such as water source 1504, brine source 1505, disinfectant source 1506, and base source 1507. The recharger has a zirconium phosphate receiving compartment 1503 and a zirconium oxide receiving compartment 1502. The recharger also has one or more pumps and valves (not shown in FIG. 15) for selectively delivering the recharging fluids from the fluid sources to the reusable modules. As shown in FIG. 15, the recharging fluid sources are housed external to the recharger 1501. Alternatively the recharging fluid sources can be housed within the recharger 1501. A drain line (not shown) is also connected to the recharger 1501 for disposal of waste fluids exiting the reusable modules. The drain line is fluidly connected to a drain, or alternatively, the drain line can be fluidly connected to one or more waste reservoirs for storage and later disposal.

The rechargers can be used in any setting, including a clinic, at home, or in a mobile setting. In any setting, the rechargers can use a water tank or any other source of potable or deionized water. For use in a mobile setting, vans or trucks can carry the rechargers, the disinfectant source, the brine solution, the base solution, and optionally the water, to a location for recharging. For at home use, the brine solution, disinfectant solution, base solution, and optionally the water, may be prepackaged and shipped to a patient. The patient can connect each of the sources to the recharger to allow recharging and reuse of the sorbent modules in dialysis. As described, the rechargers can provide for inline mixing of chemicals, reducing the amount of chemicals required to be moved for use in a mobile setting. Inline mixing of chemicals allows for a smaller amount of concentrated solutions to be moved to a location in a mobile or at home setting, and water from a local water source, such as municipal drinking water, can dilute the disinfectant, base, and/or brine inline. Alternatively, a deionized or purified water source can be provided in a mobile setting. Effluent from the sorbent modules can be collected and neutralized inline for immediate disposal in any drain, or can be collected for later neutralization and disposal offline. The ability to neutralize and dispose of the combined effluents in a drain allow for easier use in an at home or mobile setting, without the need for large waste reservoirs and further treatment.

Figure 16:
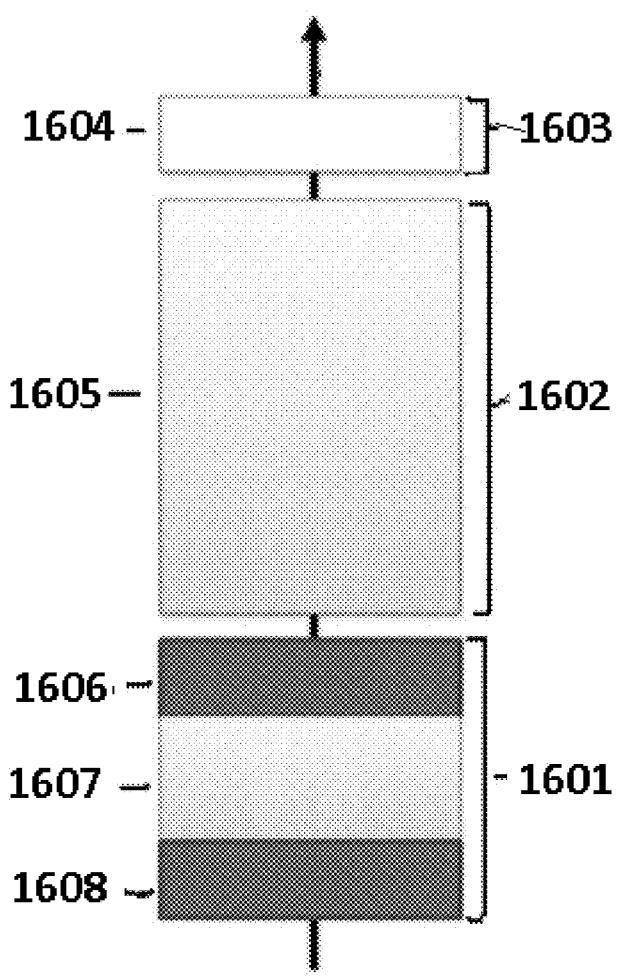
FIG. 16 shows material layers in a module sorbent cartridge including reusable modules.

A non-limiting embodiment of a reusable sorbent cartridge having modules that can be separated and recharged by systems and methods of the present invention is shown in FIG. 16. The sorbent cartridge can be separated into reusable modules to facilitate recharging of one or more sorbent materials. In FIG. 16, the sorbent cartridge has a first sorbent module 1601, a second sorbent module 1602, and a third sorbent module 1603. The first module 1601 can have a layer of activated carbon 1608, a layer of alumina and urease 1607, and a second layer of activated carbon 1606. The activated carbon can remove many non-ionic solutes from the dialysate. The urease catalyzes the conversion of urea in the dialysate into ammonium ions. The alumina can serve as a support for the urease. The second layer of activated carbon 1606 can capture any urease that migrates out of alumina and urease layer 1607 prior to exiting the first module 1601. The first module 1601 can be a single use module, or can be a multiple use module with replenishment of the urease. The second module 1602 can have zirconium phosphate 1605. After dialysis, zirconium phosphate 1605 will contain bound potassium, calcium, magnesium, and ammonium ions, which can be replaced with sodium and hydrogen ions by the recharging process described herein. Third module 1603 can contain zirconium oxide 1604. After use, the zirconium oxide 1604 will contain bound phosphate, fluoride and other anions, which can be replaced with hydroxide anions through the recharging process described herein. The flow direction of flow of dialysate through the sorbent cartridge is shown by the arrow in FIG. 16. The recharging solutions can also flow through the reusable sorbent modules in an opposite direction to improve the efficiency of the recharging process.

Figure 17:
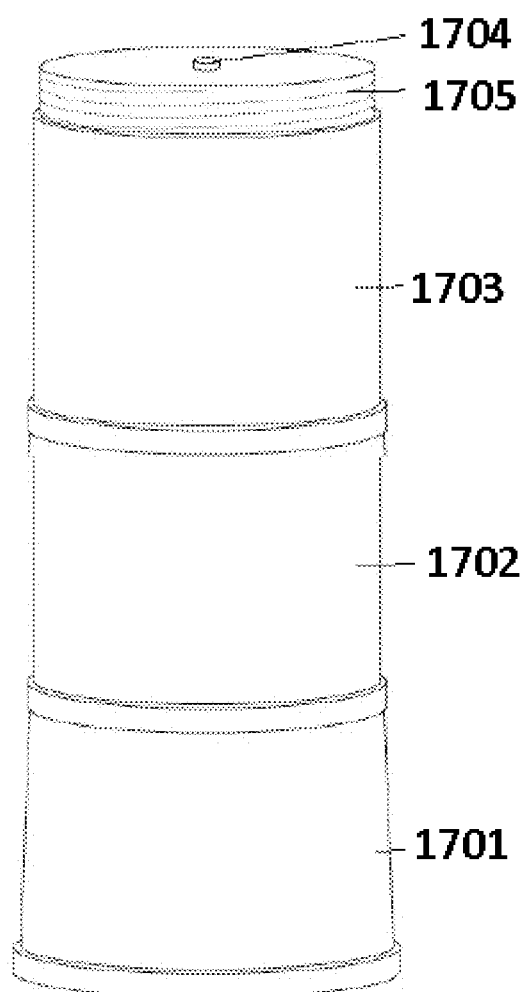
FIG. 17 shows multiple sorbent modules connected together to form a sorbent cartridge.

FIG. 17 illustrates another non-limiting example of a modular sorbent cartridge that can be used in the recharging process described herein. The modular sorbent cartridge can be separated into discrete modules including a first module 1701, a second module 1702, and a third module 1703 connected together to form a sorbent cartridge. The first module 1701 can contain activated carbon, urease, and alumina; the second module 1702 can contain zirconium phosphate; and the third module 1703 can contain zirconium oxide. One of skill in the art will understand that the modular sorbent cartridge illustrated in FIG. 17 is for illustrative purposes only, and modifications to the sorbent cartridge can be made within the scope of the invention. Alternatively, the sorbent modules can be independent with fluid lines connecting each of the sorbent modules for dialysis. During dialysis, dialysate can enter the sorbent cartridge through the bottom of first module 1701, travel through modules 1701, 1702, and 1703, and exit through fluid outlet 1704. The fluid outlet 1704 can connect to the rest of the dialysate flow path. Threaded portion 1705 on module 1703 can connect modules to each other, to the dialysate flow path, or to the recharger as described herein. The threaded portion 1705 can be included on any of the sorbent modules. Other connection types suitable for secured fluid connection in dialysis known in the art is contemplated by the invention. For example, fluid lines can be clamped directly onto fluid outlet 1704. After dialysis, a user can disconnect the sorbent modules for disposal of single use modules and for recharging of the reusable modules.

One skilled in the art will understand that various combinations and/or modifications and variations can be made in the described systems and methods depending upon the specific needs for operation. Moreover features illustrated or described as being part of an aspect of the invention may be used in the aspect of the invention, either alone or in combination.

We claim:
1. A sorbent recharger, comprising:
   a first receiving compartment for a first sorbent module; the receiving compartment having a first sorbent module inlet and a first sorbent module outlet;
   a first inlet line fluidly connected to the first sorbent module inlet;
   wherein the first inlet line is fluidly connected to at least one of a disinfectant source, a brine source, a base source, and a water source;
   a first effluent line fluidly connected to the first sorbent module outlet;
   at least a first pump positioned in the first inlet line for pumping fluid from the disinfectant source, brine source, and water source to the first sorbent module inlet;
   at least one flow sensor, at least one pressure sensor, at least one temperature sensor, and at least one conductivity sensor; and
   a control system in communication with at least one of the flow sensor, pressure sensor, temperature sensor or conductivity sensor;
   wherein the control system controls the first pump by determining whether at least one of the pressure, flow rate, temperature, and conductivity are within predetermined ranges.

2. The sorbent recharger of claim 1, further comprising a user interface in communication with the control system.

3. The sorbent recharger of claim 1, wherein at least one conductivity sensor is located upstream of the first sorbent module inlet;
   wherein the control system controls the first pump by determining whether at least the pressure, the flow rate, and the conductivity are within predetermined ranges; and wherein
   the control system generates an alert indicating a leak when the pressure is below the predetermined range; and wherein the control system generates an alert indicating an occlusion when the pressure is above the predetermined range;
   wherein the control system generates an alert indicating a pump failure when the flow rate is below the predetermined range and the conductivity of a fluid upstream of the first sorbent module inlet is within a predetermined range; and
   wherein the control system generates an alert indicating a chemical run-out when the control system determines the flow rate is below the predetermined range and that the conductivity of the fluid upstream of the first sorbent module inlet is below the predetermined range.

4. The sorbent recharger of claim 1, further comprising a heater in the first inlet line, the at least one temperature sensor in communication with the control system; wherein the control system controls the heater based on data from the at least one temperature sensor; wherein the control system generates an alert if the temperature in the first inlet line does not reach a predetermined temperature in a predetermined amount of time.

5. The sorbent recharger of claim 4, further comprising a second temperature sensor in the first effluent line, wherein the control system generates an alert if the temperature in the first effluent line does not reach a predetermined temperature in a predetermined amount of time; wherein the first inlet line is fluidly connected to the at least one brine source, and the control system calculates an amount of brine necessary for recharging a sorbent module containing zirconium phosphate based, at least in part, on the temperature in the first effluent line.

6. The sorbent recharger of claim 1, further comprising a second receiving compartment for a second sorbent module; the second receiving compartment having a second sorbent module inlet and a second sorbent module outlet;
   a second inlet line fluidly connected to the second sorbent module inlet;
   a second effluent line fluidly connected to the second sorbent module outlet;
   wherein at least one of the disinfectant source, the base source, and the water source are fluidly connected to the second inlet line;
   at least a second pump positioned in the second inlet line for pumping fluid from at least one of the disinfectant source, the base source, and the water source to the second sorbent module inlet;
   at least one flow sensor, at least one pressure sensor, at least one temperature sensor, and at least one conductivity sensor positioned in the second inlet line;
   wherein the control system is in communication with at least one of the flow sensor, pressure sensor, temperature sensor, and conductivity sensor; the control system controlling the second pump.

7. The sorbent recharger of claim 6, wherein at least one conductivity sensor is positioned in the first effluent line; wherein the control system controls the first pump, the second pump, or both pumps to pump fluid from the disinfectant source, brine source, and/or water source through the first sorbent module; and wherein the control system determines a conductivity of fluid in the first effluent line based on data from the conductivity sensor positioned in the first effluent line;
   wherein at least one conductivity sensor is positioned in the second effluent line; wherein the control system controls the first pump, the second pump, or both pumps to pump fluid from the disinfectant source, base source, and/or water source through the second sorbent module; and wherein the control system determines a conductivity of fluid in the second effluent line based on data from the conductivity sensor positioned in the second effluent line.

8. The sorbent recharger of claim 7, wherein the second effluent line is fluidly connected to the first effluent line at a junction; and further comprising a static mixer at or downstream of the junction;
   wherein the control system calculates a neutralization ratio based on the conductivity of the fluid in the first effluent line and the conductivity of the fluid in the second effluent line; and wherein the control system controls the second pump and the first pump based on data from the conductivity sensor in the first effluent line and the conductivity sensor in the second effluent line; wherein
   the control system controls the first pump and second pump to generate a fluid within a predetermined pH range in the static mixer based on the neutralization ratio.

9. The sorbent recharger of claim 8, wherein the control system stops the second pump when the conductivity of the fluid in the second effluent line reaches a predetermined range; and
   wherein the control system stops the first pump when the conductivity of the fluid in the first effluent line reaches a predetermined range.

10. The sorbent recharger of claim 9, wherein the control system starts the first pump and second pump when the conductivity in the first effluent line reaches a predetermined range.

11. The sorbent recharger of claim 5, wherein the control system calculates an amount of brine necessary for recharging a sorbent module containing zirconium phosphate based, at least in part, on the temperature in the first effluent line.

12. A method, comprising the steps of:
pumping fluid from a disinfectant source, a base source, a brine source, a water source, or combinations thereof, through a recharging flow path to a first sorbent module; and
determining a presence of at least one of a leak, occlusion, pump failure, chemical mismatch, or chemical run-out.

13. The method of claim 12, wherein determining the presence of a leak comprises determining that a pressure in the recharging flow path is below a predetermined range;
wherein determining the presence of an occlusion comprises determining that a pressure in the recharging flow path is above a predetermined range;
wherein determining the presence of a pump failure comprises the steps of determining that a flow rate in the recharging flow path is below a predetermined range; and determining that a conductivity at a sorbent module inlet of the first sorbent module is within a predetermined range; and
wherein determining the presence of a chemical run-out comprises the steps of determining that a flow rate in the recharging flow path is below a predetermined range; and
determining that a conductivity at a sorbent module inlet of the first sorbent module is below a predetermined range.

14. The method of claim 12, further comprising the steps of pumping fluid from a disinfectant source, a base source, a brine source, a water source, or combinations thereof through the recharging flow path to a second sorbent module; and
pumping fluid through a first effluent line fluidly connected to the first sorbent module and a second effluent line fluidly connected to the second sorbent module to a static mixer or a common reservoir;
determining a conductivity of a fluid in the first effluent line and determining a conductivity of a fluid in the second effluent line; and
calculating a neutralization ratio based on a conductivity of fluid in the first effluent line and the second effluent line;
wherein the step of pumping fluid from the first effluent line and the second effluent line to the static mixer or common reservoir comprises controlling a flow rate of the fluid in the first effluent line and second effluent line based on the neutralization ratio to generate a fluid in the static mixer or common reservoir within a predetermined pH range.

15. The method of claim 12, further comprising the step of:
determining a temperature of the fluid; wherein the fluid is a brine solution in a first effluent line fluidly connected to the first sorbent module;
calculating an amount of the brine solution necessary for recharging zirconium phosphate wherein the first sorbent module contains zirconium phosphate based, at least in part, on the temperature in the first effluent line.

16. The method of claim 12, further comprising the steps of:
pumping fluid from the disinfectant source into the first sorbent module;
determining a conductivity in a first effluent line; and
stopping the step of pumping the fluid from the disinfectant source if the conductivity in the first effluent line is within a predetermined range.

17. The method of claim 16, further comprising the step of pumping water from the water source into the first sorbent module at a predetermined time after the step of stopping the pumping of fluid from the disinfectant source.

18. The method of claim 16, further comprising the step of venting the first sorbent module at a predetermined time after stopping pumping of fluid from the disinfectant source.

19. The method of claim 18, further comprising the step of pumping fluid from the disinfectant source into the first sorbent module while venting the first sorbent module.

* * * * *